(12) United States Patent
Arai

(10) Patent No.: US 8,663,097 B2
(45) Date of Patent: Mar. 4, 2014

(54) INSERTION DEVICE

(75) Inventor: Keiichi Arai, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/608,299

(22) Filed: Sep. 10, 2012

(65) Prior Publication Data

US 2013/0096384 A1   Apr. 18, 2013

Related U.S. Application Data

(63) Continuation of application No. PCT/JP2012/052896, filed on Feb. 8, 2012.

(30) Foreign Application Priority Data

Mar. 8, 2011  (JP) .................................. 2011-050535
Mar. 8, 2011  (JP) .................................. 2011-050536

(51) Int. Cl.
  *A61B 1/00*  (2006.01)
(52) U.S. Cl.
  USPC ......... 600/144; 600/146; 600/149; 604/95.04
(58) Field of Classification Search
  CPC . A61B 1/00078; A61B 1/0055; A61B 1/0057
  USPC .......... 600/139, 141, 144, 146, 148, 149, 150
  See application file for complete search history.

(56) References Cited

U.S. PATENT DOCUMENTS 3,058,473 A * 10/1962 Whitehead .................. 604/95.04
4,006,681 A *  2/1977 Grace et al. .................... 101/111
4,557,254 A * 12/1985 Yamaguchi .................... 600/149
4,762,118 A *  8/1988 Lia et al. ........................ 600/141
4,762,119 A *  8/1988 Allred et al. .................. 600/149
4,815,478 A *  3/1989 Buchbinder et al. .......... 600/585
5,441,483 A *  8/1995 Avitall ........................ 604/95.05
5,483,952 A *  1/1996 Aranyi .......................... 600/131

(Continued)

FOREIGN PATENT DOCUMENTS

| EP | 2 127 591 A1 | 12/2009 |
| JP | S56-36935 | 4/1981 |
| JP | S58-41524 | 3/1983 |
| JP | 09-108176 | 4/1997 |

OTHER PUBLICATIONS

Extended Supplementary European Search Report dated Sep. 23, 2013 from related European Application No. 12 75 4887.3.

*Primary Examiner* — Anhtuan T Nguyen
*Assistant Examiner* — Jae Woo
(74) *Attorney, Agent, or Firm* — Scully, Scott, Murphy & Presser, P.C.

(57) ABSTRACT

An insertion device includes: a linear member inserted into an insertion portion to be movable; a plurality of mobile bodies provided in a state of being strung together on an outer periphery of the linear member and being movable with respect to the linear member; a restricting member fixed with respect to the linear member, the restricting member restricting a movable range of each mobile body with respect to the linear member and preventing each of the mobile bodies from falling off; and a fixing pin being movable between a first position and a second position at which the fixing pin is fitted in between any adjacent two mobile bodies.

13 Claims, 18 Drawing Sheets

(56) References Cited

U.S. PATENT DOCUMENTS

| | | | |
|---|---|---|---|
| 5,531,664 A * | 7/1996 | Adachi et al. | 600/149 |
| 6,440,062 B1 * | 8/2002 | Ouchi | 600/146 |
| 6,540,725 B1 * | 4/2003 | Ponzi | 604/272 |
| 6,575,931 B1 * | 6/2003 | Ponzi | 604/95.01 |
| 6,730,058 B2 * | 5/2004 | Hayzelden | 604/95.04 |
| 7,708,756 B2 * | 5/2010 | Nobis et al. | 606/205 |
| 7,789,822 B2 * | 9/2010 | Suzuki | 600/104 |
| 7,862,503 B2 * | 1/2011 | Smith et al. | 600/104 |
| 8,221,305 B2 * | 7/2012 | Suzuki | 600/106 |
| 8,308,634 B2 * | 11/2012 | Torii | 600/149 |
| 2002/0165484 A1 * | 11/2002 | Bowe et al. | 604/95.05 |
| 2002/0165485 A1 * | 11/2002 | Simpson et al. | 604/95.05 |
| 2003/0014010 A1 * | 1/2003 | Carpenter et al. | 604/117 |
| 2005/0261549 A1 * | 11/2005 | Hewit et al. | 600/114 |
| 2006/0069311 A1 | 3/2006 | Sullivan et al. | |
| 2007/0244355 A1 * | 10/2007 | Shaw | 600/107 |
| 2008/0086031 A1 * | 4/2008 | Mitsuya | 600/149 |
| 2008/0188868 A1 | 8/2008 | Weitzner et al. | |
| 2008/0262309 A1 * | 10/2008 | Miyoshi et al. | 600/146 |
| 2010/0280320 A1 * | 11/2010 | Alvarez et al. | 600/146 |
| 2012/0041264 A1 * | 2/2012 | Blase | 600/121 |
| 2012/0053417 A1 * | 3/2012 | Yamakawa et al. | 600/144 |
| 2013/0035548 A1 * | 2/2013 | Ianchulev | 600/120 |
| 2013/0096384 A1 * | 4/2013 | Arai | 600/144 |

* cited by examiner

INSERTION DEVICE

CROSS REFERENCE TO RELATED APPLICATION

This application is a continuation application of PCT/JP2012/052896 filed on Feb. 8, 2012 and claims benefit of Japanese Applications No. 2011-050535 filed in Japan on Mar. 8, 2011, No. 2011-050536 filed in Japan on Mar. 8, 2011, the entire contents of each of which are incorporated herein by their reference.

BACKGROUND OF THE INVENTION

1. Field of the Invention

The present invention relates to an insertion device including an elongated insertion portion to be inserted into a subject.

2. Description of the Related Art

Recently, insertion devices having an insertion portion to be inserted into a subject, for example, endoscopes, have been widely used in a medical field and an industrial field.

An endoscope used in the medical field is able to observe an organ in a body cavity by inserting an elongated insertion portion into the body cavity, which is the subject, and perform various treatments by using a treatment instrument which is inserted into an insertion channel for the treatment instrument included in the endoscope as desired.

Further, an endoscope used in the industrial field is able to perform inspections such as observation and various treatments of flaws, corrosion and the like of an area to be inspected in an object by inserting an elongated insertion portion of the endoscope into an object such as a jet engine and a factory piping.

Here, the insertion portion of the endoscope is provided with a linear member which is movable forwards and backwards in the insertion direction of the insertion portion.

To be specific, examples of the linear member provided in the insertion portion of an endoscope include a bending wire which is pulled/released to cause a bending portion provided at a distal end side in the insertion direction (hereinafter, simply referred to as a "distal end side") of the insertion portion to be bent in multiple directions, and a coil sheath for covering the outer periphery of the bending wire.

Further, examples of the linear member include: a coil pipe wire provided in a coil pipe for making the rigidity of a flexible tube portion variable, which is located more rearward in the insertion direction (hereinafter, simply referred to as "rearward") than a bending portion in an insertion portion, and to be pulled/released to make the rigidity of the coil pipe variable; and an operation wire to be pulled/released for a raising or lowering operation of a treatment instrument elevator in a distal end portion located more forward in the insertion direction (hereinafter, simply referred to as "forward") than a bending portion of an insertion portion.

Further, as an example of the configuration in which the position of a linear member that moves forwards and backwards in the insertion direction is fixed in the insertion direction, Japanese Patent Application Laid-Open Publication No. 9-108176 discloses a configuration for fixing the position of the above-described coil pipe wire.

Specifically, Japanese Patent Application Laid-Open Publication No. 9-108176 discloses a fixing mechanism in which a rack formed with a plurality of grooves along an insertion direction is provided at a proximal end in the insertion direction (hereinafter, simply referred to as a "proximal end") of a coil pipe wire, and a pinion gear of a hole portion which rotates with an operation knob engages with the rack so that when the operation knob is rotated in one direction, the engagement position of the pinion gear with respect to the plurality of grooves of the rack is shifted forward, that is, by resisting a releasing force of the coil pipe wire by utilizing the engagement between the grooves of the rack and the pinion gear in a configuration in which the rack is moved rearward to pull the coil pipe wire, the position of rack, that is, the pulling position of the coil pipe wire can be fixed, even if the hand is moved off the operation knob.

Moreover, there is a well-known configuration in which the position of a linear member is fixed by friction force by pinching a proximal end side in the insertion direction (hereinafter, simply referred to as a "proximal end side") of a linear member between two friction members.

SUMMARY OF THE INVENTION

An insertion device according to an aspect of the present invention is an insertion device including an elongated insertion portion to be inserted into a subject, including: a linear member inserted into the insertion portion and movable forwards and backwards in an insertion direction of the insertion portion; a plurality of mobile bodies provided in a state of being strung together on an outer periphery of the linear member along the insertion direction, the mobile bodies being movable forwards and backwards in the insertion direction with respect to the linear member; a restricting member fixed with respect to the linear member, the restricting member restricting a movable range of each of the mobile bodies with respect to the linear member, and preventing each of the mobile bodies from falling off from the linear member; and a fixing pin being movable between a first position separated from the plurality of mobile bodies, and a second position at which the fixing pin is fitted in between any two of the mobile bodies adjacent to each other in the insertion direction, and being fixed in position in the insertion direction after being fitted in between the mobile bodies at the second position, the fixing pin being formed such that a diameter of an area to be fitted in between the mobile bodies coincides with the movable range of the mobile bodies.

DETAILED DESCRIPTION OF THE PREFERRED EMBODIMENTS

Hereafter, embodiments of the present invention will be described with reference to the drawings. Note that drawings are schematic, and the relationship between the thickness and width of each member, the ratios of thicknesses of respective members, and the like may be different from actual ones; and it is without saying that portions may be included of which dimensional relations and ratios are mutually different even between respective drawings.

Hereinafter the insertion device will be described taking an example of an endoscope.

Figure 1:
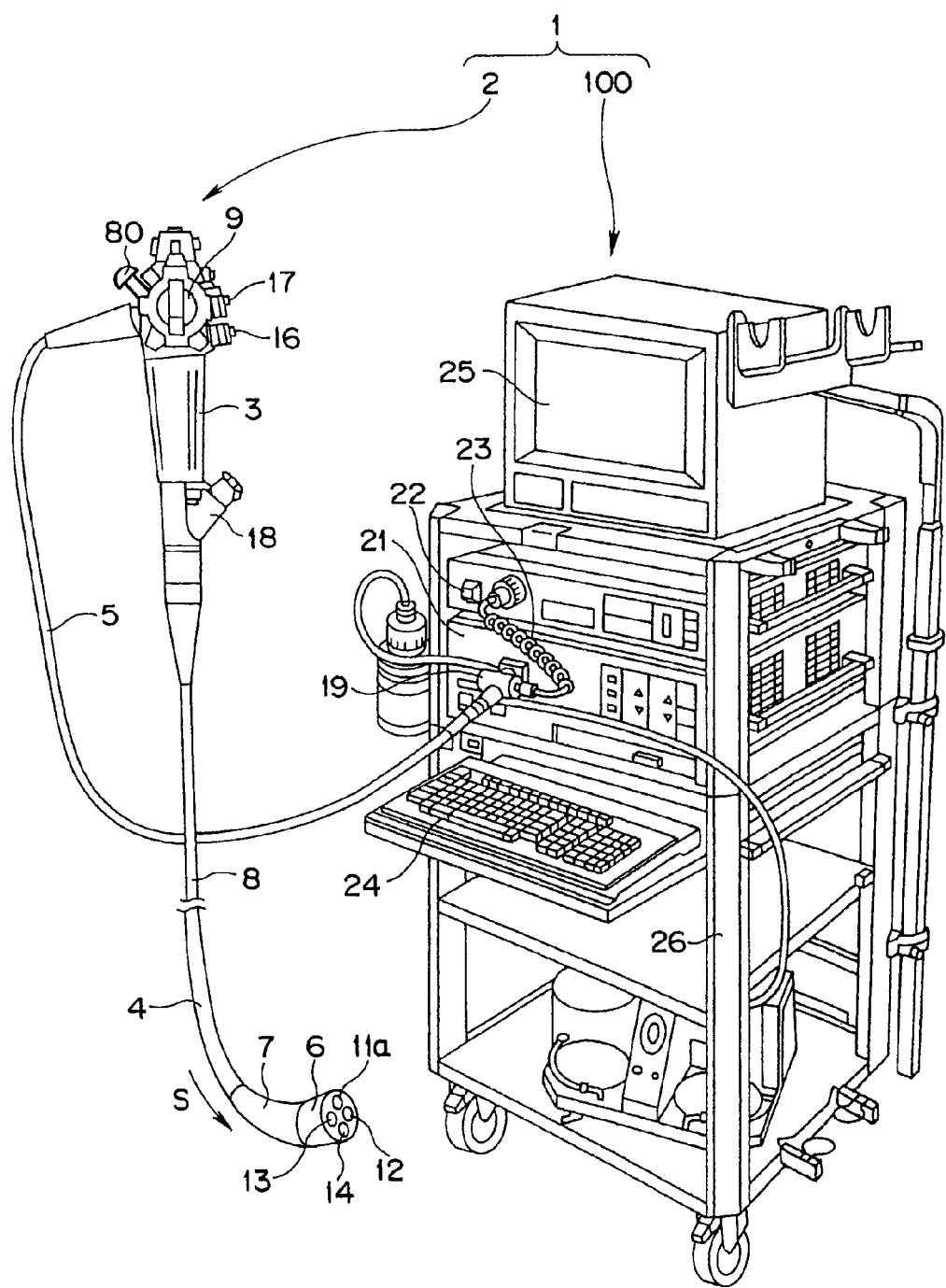
FIG. 1 is a perspective view showing the exterior of an endoscope apparatus including an endoscope of the present embodiment.

FIG. 1 is a perspective view showing the exterior of an endoscope apparatus including an endoscope showing the present embodiment.

As shown in FIG. 1, the principal part of an endoscope apparatus 1 is made up of an endoscope 2 which is an insertion device, and a peripheral apparatus 100. The principal part of the endoscope 2 is made up of an operation section 3, an insertion portion 4 to be inserted into a subject, a universal cord 5, and a connector 19.

The principal part of the peripheral apparatus 100 is made up of a light source apparatus 21, a video processor 22, a connection cable 23, a keyboard 24, and a monitor 25, arranged in a cradle 26. Further, the endoscope 2 and the peripheral apparatus 100, which have such configurations, are connected with each other by the connector 19.

The operation section 3 of the endoscope 2 is provided with a bending operation knob 9, an air/water supply operation button 16, a suction operation button 17, a treatment instrument insertion port 18, and a fixing lever 80 to be described later.

The insertion portion 4 of the endoscope 2 is made up of a distal end portion 6, a bending portion 7, and a flexible tube portion 8, and is formed into an elongated shape along the insertion direction S.

The bending portion 7 is operated to be bent by the bending operation knob 9 provided in the operation section 3, and is provided between the distal end portion 6 and the flexible tube portion 8 on the distal end side of the insertion portion 4 so as to be made bendable in, for example, four directions of up and down, and left and right when the below described four wires $30u$, $30d$, $30r$, $30l$ (see FIG. 15), which are inserted into the insertion portion 4, are pulled/released by bending operation of the operation knob 9.

Note that the bending portion 7 may be configured to be bendable by means of, for example, a rod or the like that is moved by a motor or the like without being limited to the four wires.

In a distal end face of the distal end side of the distal end portion 6, an objective lens 11a in an image pickup unit provided in the distal end portion 6 and not shown; as well as a distal end opening 12 of a channel not shown and for supplying fluid toward an area to be inspected in a subject; an illumination window 13 for illuminating inside the subject; and a distal end opening 14 of a treatment instrument insertion channel not shown are provided.

From the distal end opening 12, gas and liquid are selectively ejected by a button operation of the air/water supply operation button 16 of the operation section 3. From the distal end opening 14, mucus and the like in the body cavity is selectively collected through the treatment instrument insertion channel by a button operation of the suction operation button 17 of the operation section 3, and besides, various treatment instruments which are inserted from the treatment instrument insertion port 18 are projected toward the area to be inspected.

The connector 19 is provided at the distal end of the universal cord 5 of the endoscope 2, and the connector 19 is connected to the light source apparatus 21 of the peripheral apparatus 100. The connector 19 is provided with various tube sleeves not shown and various electrical contacts, and is electrically connected with a video processor 22 via a connection cable 23.

Figure 2:
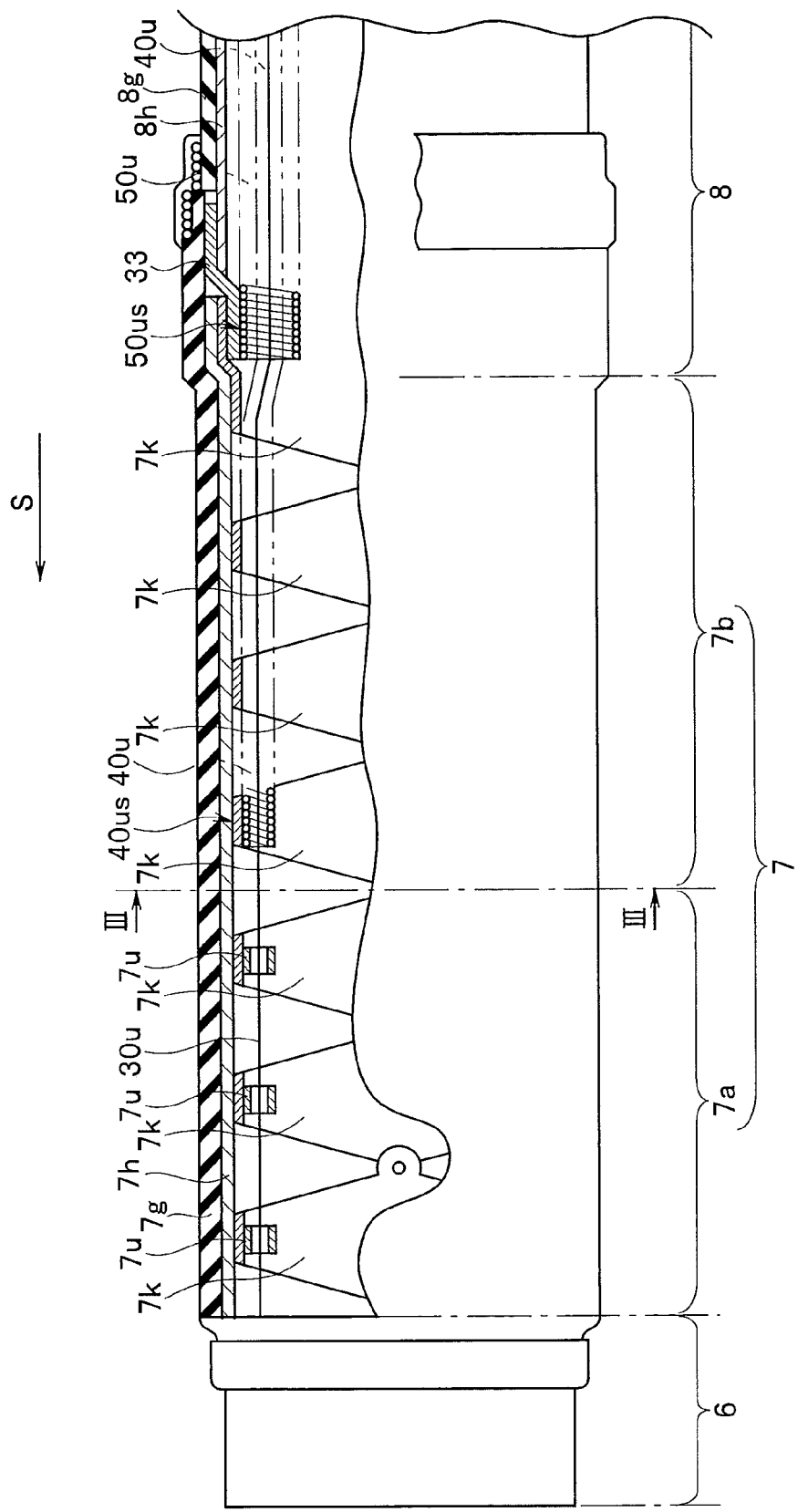
FIG. 2 is a partial sectional view schematically showing an internal configuration of a distal end side of an insertion portion of FIG. 1.
Figure 3:
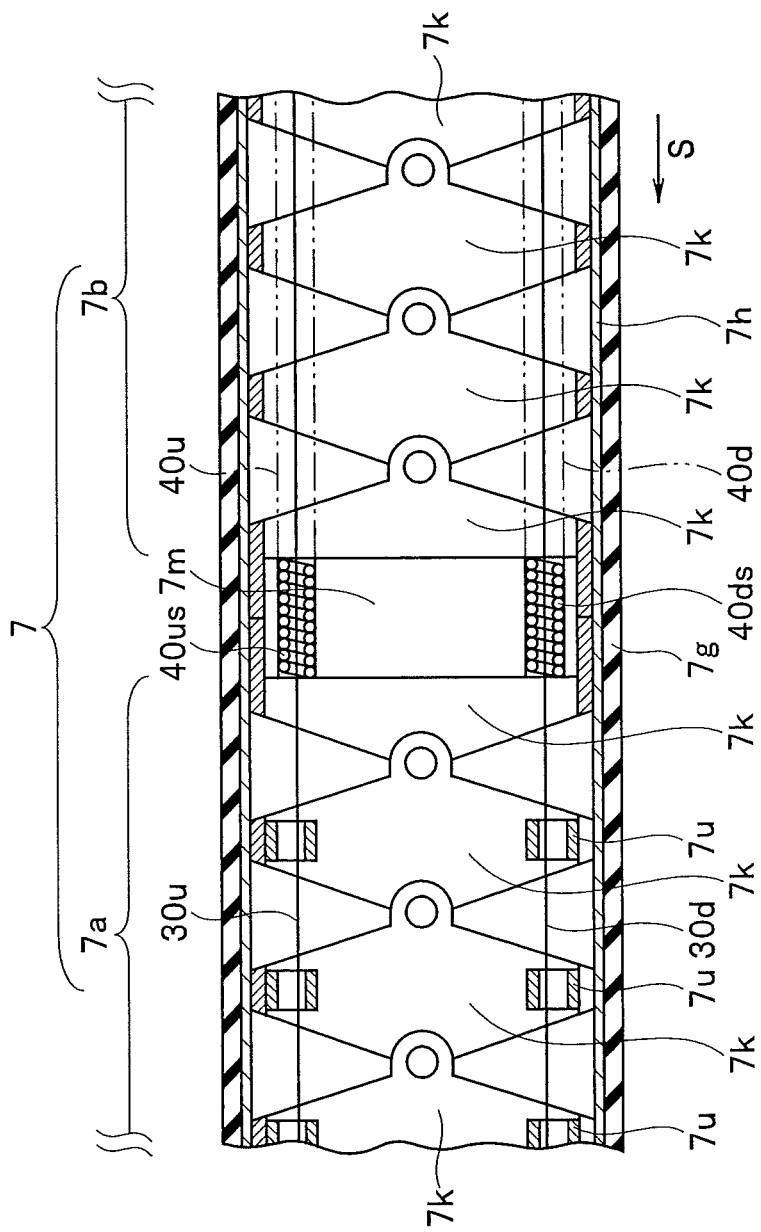
FIG. 3 is a partial sectional view showing a modification in which a first area and a second area in the bending portion of FIG. 2 are connected with a tube sleeve connector.

Next, configurations inside the operation section 3 and the insertion portion 4 will be described by using FIGS. 2 to 16. FIG. 2 is a partial sectional view schematically showing internal configuration of a distal end side of an insertion portion of FIG. 1, and FIG. 3 is a partial sectional view showing a modification in which a first area and a second area in the bending portion of FIG. 2 are connected with a tube sleeve connector.

Figure 4:
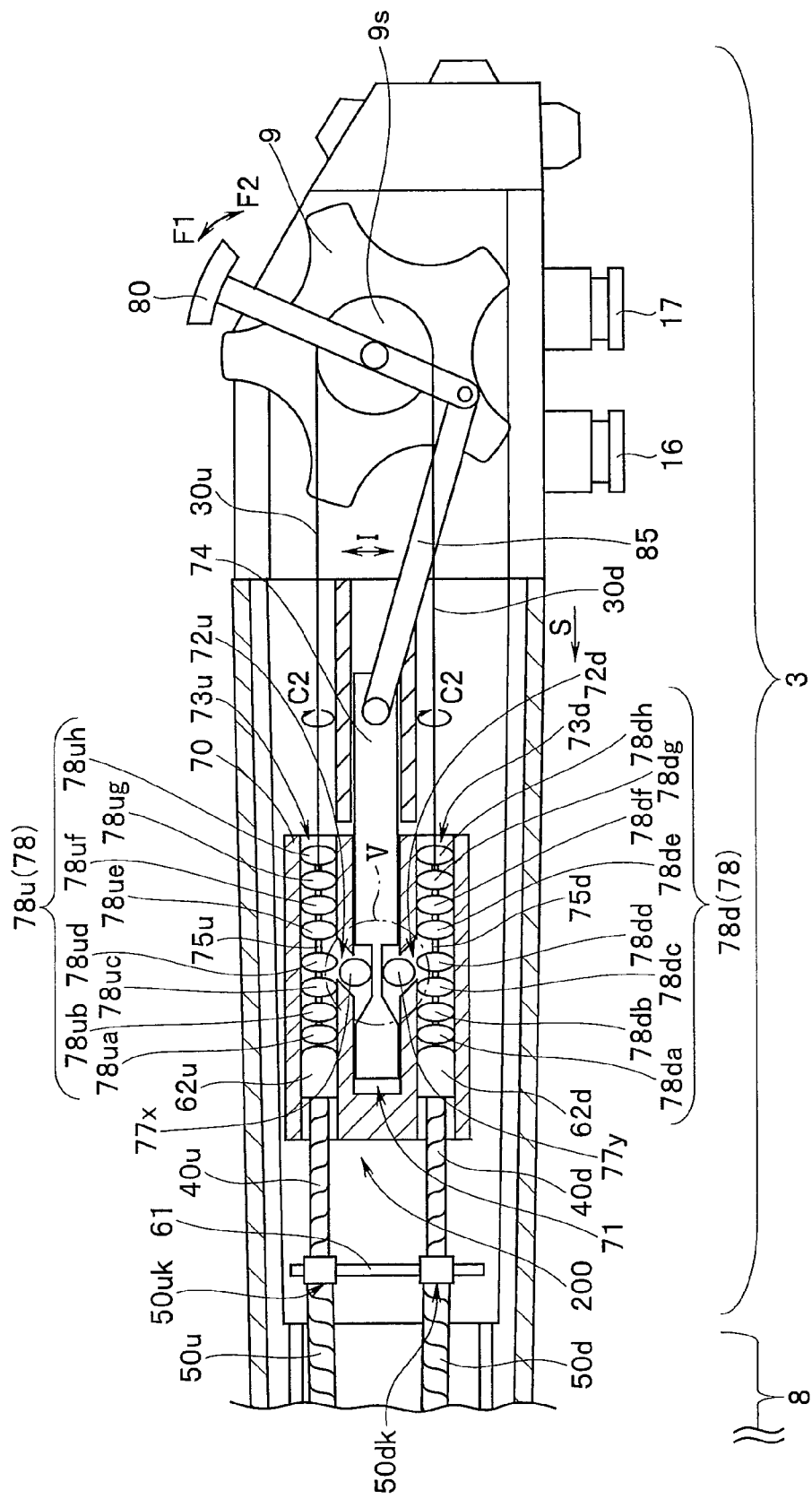
FIG. 4 is a partial sectional view schematically showing an internal configuration of an operation section of FIG. 1 along with a proximal end side of the insertion portion.
Figure 5:
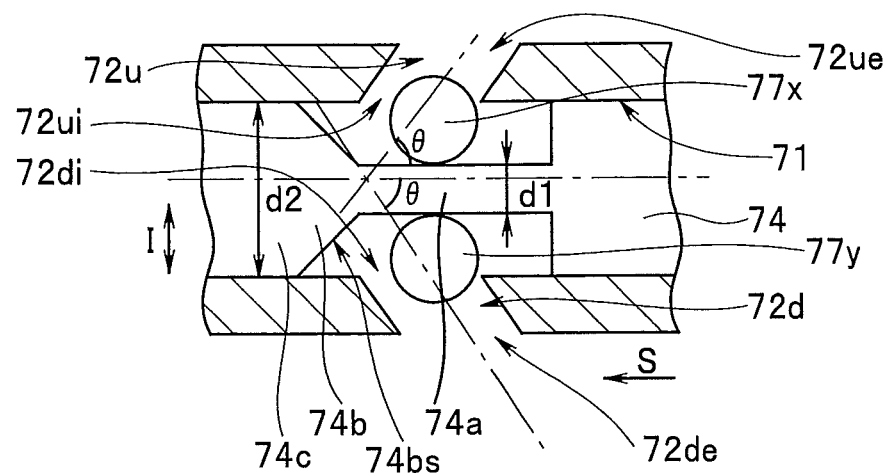
FIG. 5 is a partial sectional view enlargedly showing an area surrounded by V in FIG. 4.
Figure 6:
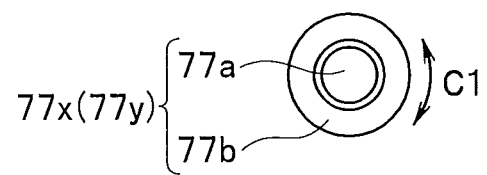
FIG. 6 is a diagram showing a fixing pin of FIG. 4.

Further, FIG. 4 is a partial sectional view schematically showing an internal configuration of an operation section of FIG. 1 along with a proximal end side of the insertion portion, FIG. 5 is a partial sectional view enlargedly showing an area surrounded by V in FIG. 4, and FIG. 6 is a diagram showing a fixing pin of FIG. 4.

Figure 7:
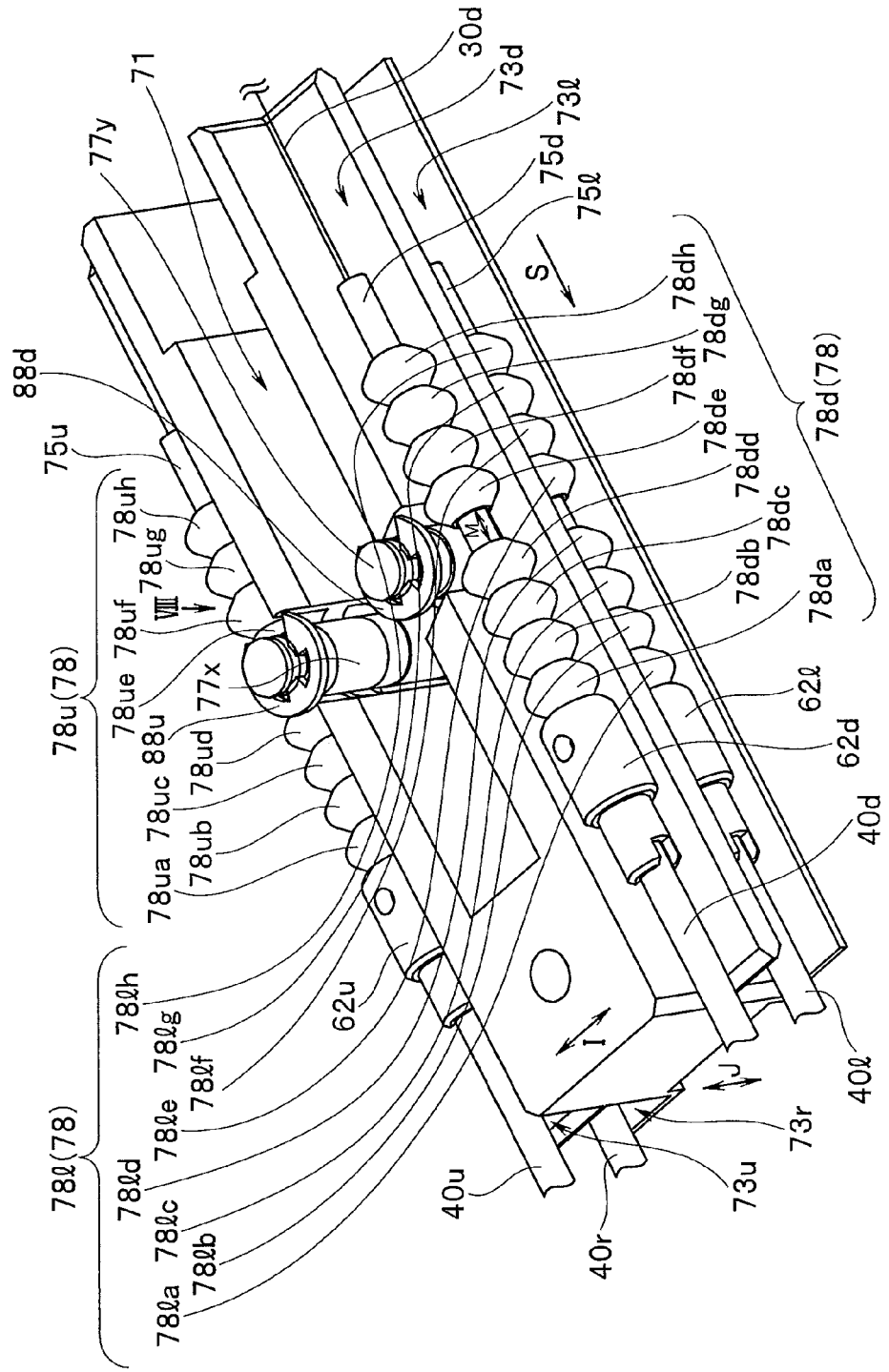
FIG. 7 is a partial perspective view enlargedly showing a fixing mechanism of FIG. 4.
Figure 8:
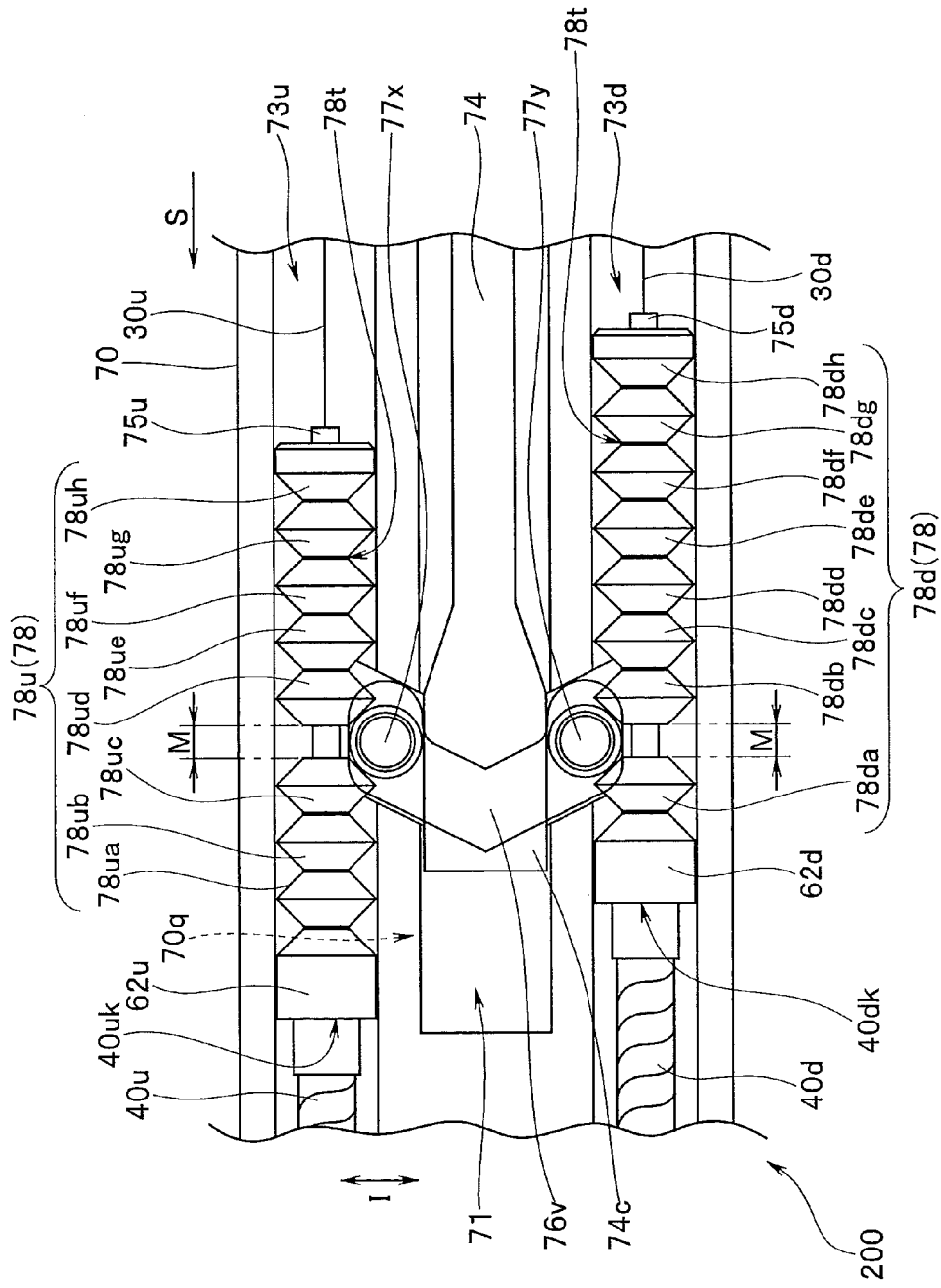
FIG. 8 is a diagram of the fixing mechanism of FIG. 7 seen from a direction VIII in FIG. 7.
Figure 9:
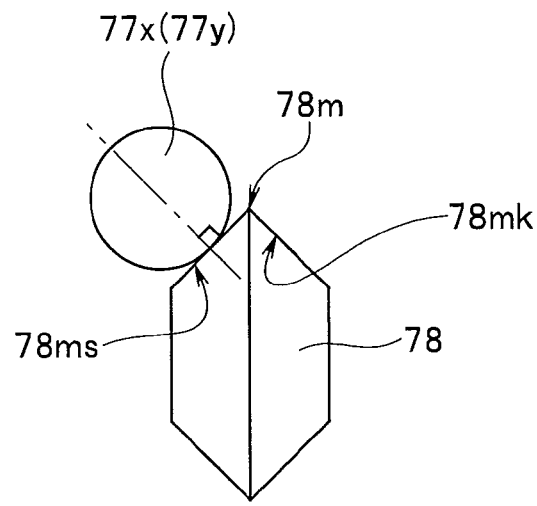
FIG. 9 is a diagram enlargedly showing a state in which a fixing pin is in abutment with a slope of a crest portion of a mobile body of FIG. 8.

Furthermore, FIG. 7 is a partial perspective view enlargedly showing a fixing mechanism of FIG. 4, FIG. 8 is a diagram of the fixing mechanism of FIG. 7 seen from a direction VIII in FIG. 7, and FIG. 9 is a diagram enlargedly showing a state in which a fixing pin is in abutment with a slope of a crest portion of a mobile body of FIG. 8.

Figure 10:
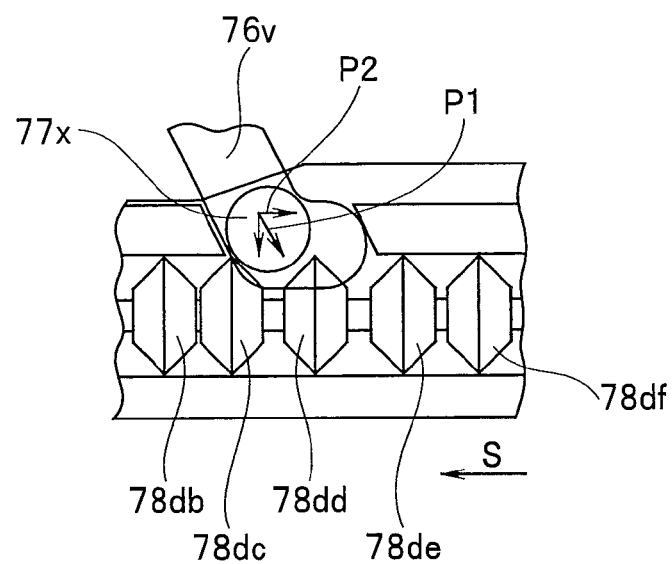
FIG. 10 is a diagram schematically showing a component force of the fixing pin in abutment with the crest portion of the mobile body of FIG. 4.
Figure 11:
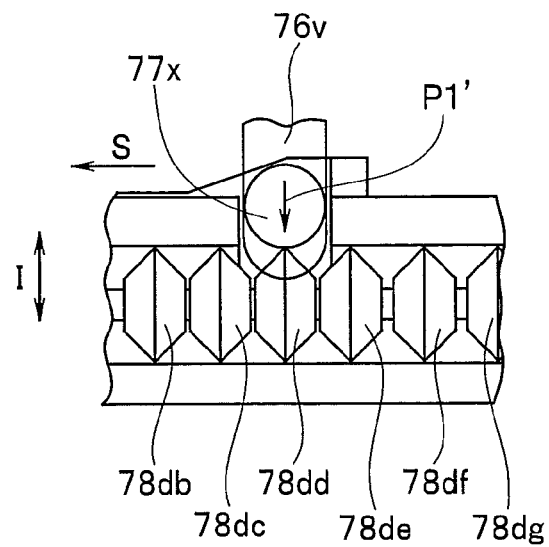
FIG. 11 is a diagram schematically showing a state in which the fixing pin is in abutment with the crest portion of the mobile body of FIG. 4 from a direction perpendicular to the insertion direction.

Moreover, FIG. 10 is a diagram schematically showing a component force of the fixing pin in abutment with the crest portion of the mobile body of FIG. 4, and FIG. 11 is a diagram schematically showing a state in which the fixing pin is in abutment with the crest portion of the mobile body of FIG. 4 from a direction perpendicular to the insertion direction.

Figure 12:
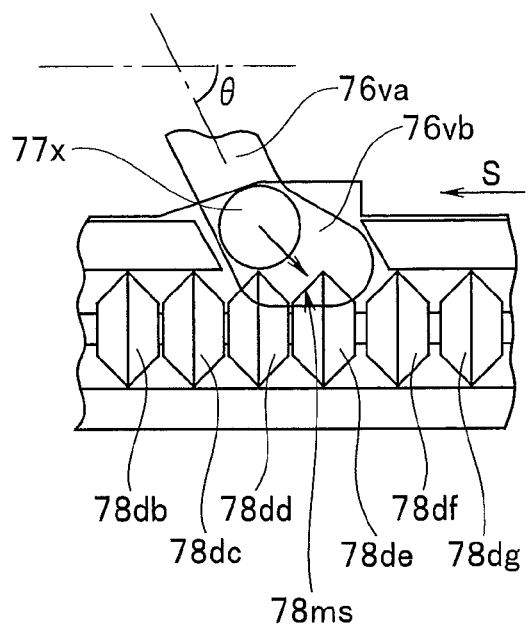
FIG. 12 is a diagram schematically showing a state in which the fixing pin is caused to slide into a rearward slope in the crest portion of a mobile body by a guide groove provided in a holding member of FIG. 8.
Figure 13:
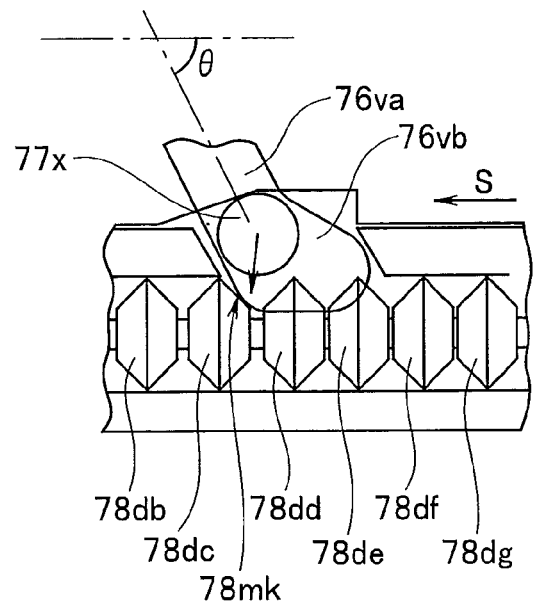
FIG. 13 is a diagram schematically showing a state in which the fixing pin is caused to slide into a forward slope in the crest portion of the mobile body by the guide groove provided in the holding member of FIG. 8.
Figure 14:
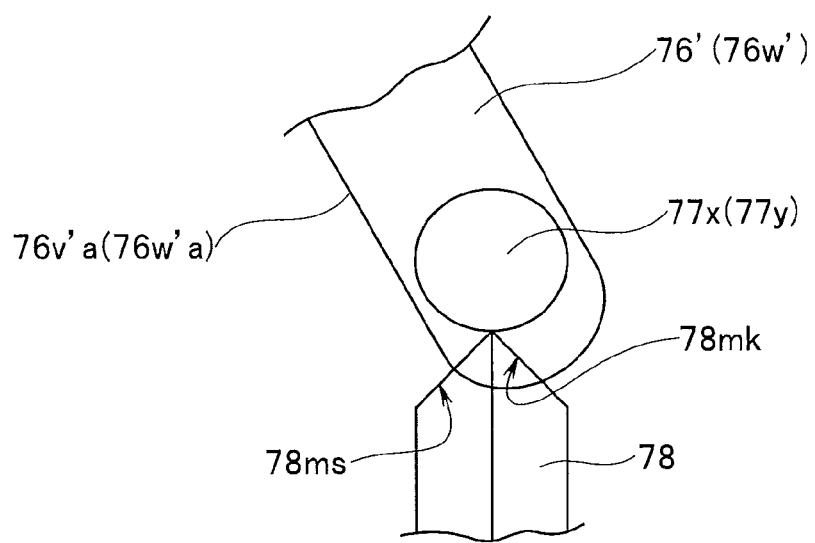
FIG. 14 is a diagram showing a different shape of the guide groove provided in the holding member of FIG. 8, along with part of the mobile body.

Further, FIG. 12 is a diagram schematically showing a state in which the fixing pin is caused to slide into a rearward slope in the crest portion of the mobile body by a guide groove provided in a holding member of FIG. 8, FIG. 13 is a diagram schematically showing a state in which the fixing pin is caused to slide into a forward slope in the crest portion of the mobile body by the guide groove provided in the holding member of FIG. 8, and FIG. 14 is a diagram showing a different shape of the guide groove provided in the holding member of FIG. 8, along with part of the mobile body.

Figure 15:
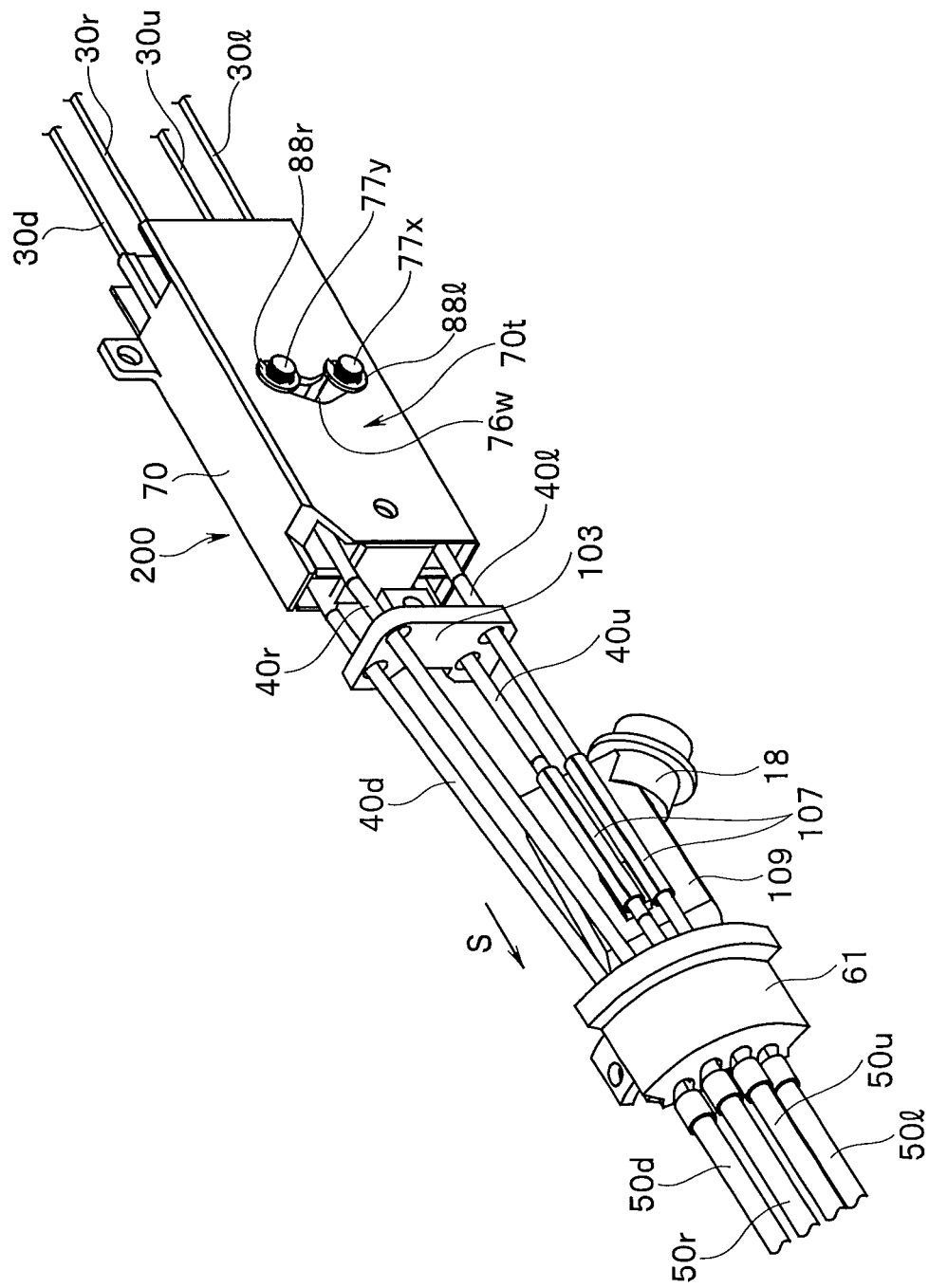
FIG. 15 is a partial perspective view of an outer coil sheath, an inner coil sheath and the fixing mechanism of FIG. 4.
Figure 16:
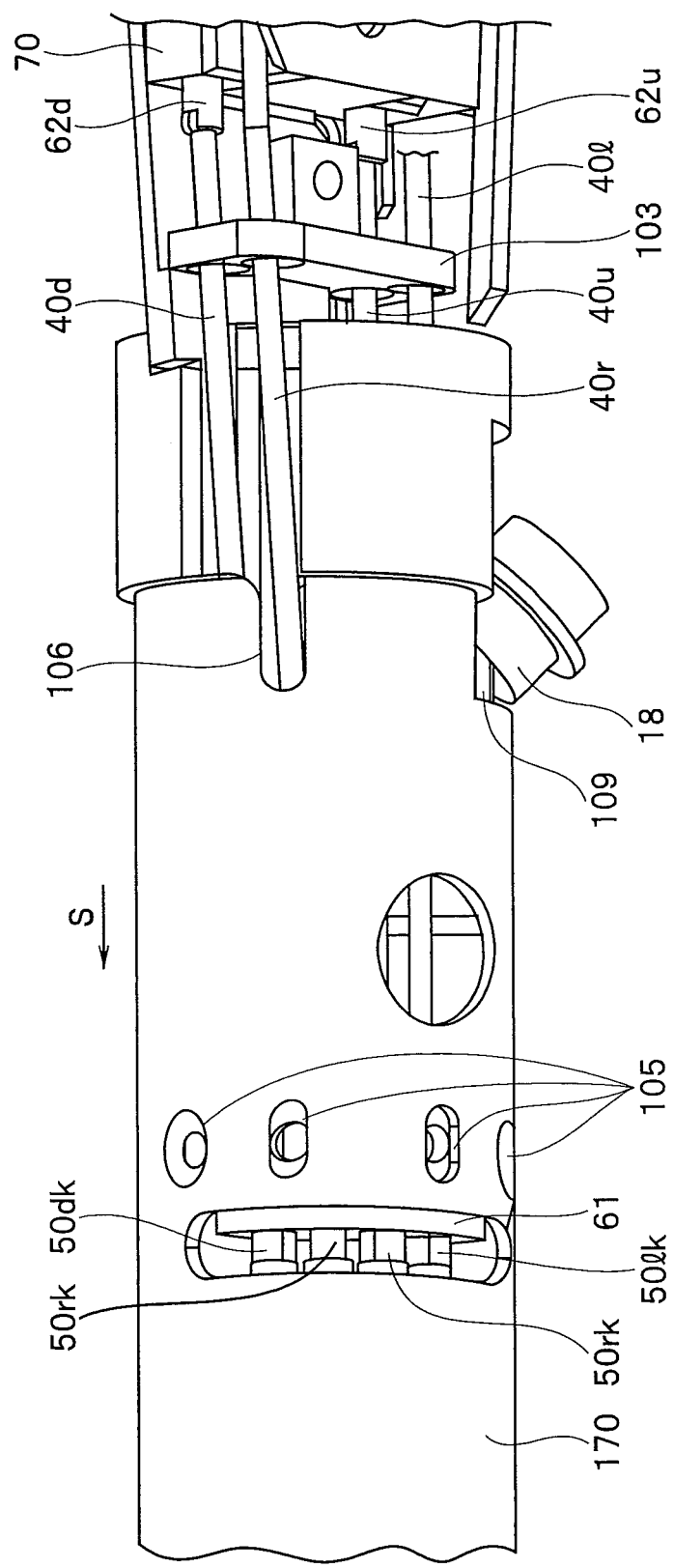
FIG. 16 is a partial perspective view showing a state in which the outer coil sheath and the inner coil sheath are covered by an outer casing.

Further, FIG. 15 is a partial perspective view of an outer coil sheath, an inner coil sheath and the fixing mechanism of FIG. 4, and FIG. 16 is a partial perspective view showing a state in which the outer coil sheath and the inner coil sheath of FIG. 15 is covered by an outer casing.

As shown in FIG. 2, a plurality of bending pieces 7*k* are provided being interconnected along the insertion direction S inside the bending portion 7. Further, the outer periphery of the plurality of bending pieces 7*k* is covered by a braid 7*h*, and the outer periphery of the braid 7*h* is covered by a bending rubber 7*g*.

Note that hereinafter, the area located in a front half part in the insertion direction S of the bending portion 7 is referred to as a first area 7*a*, and the area located in a rear half part in the insertion direction S as a second area 7*b*.

Further, as shown in FIG. 3, the bending portion 7 may have a configuration in which the first area 7*a* and the second area 7*b* are interconnected along the insertion direction S by a tube sleeve connector 7*m*.

To be specific, the bending portion 7 may have a configuration in which a bending piece 7*k* which is located closest to the proximal end side in the first area 7*a* and a bending piece 7*k* which is located closest to the distal end side in the second area 7*b* are fitted onto the outer periphery of a tube sleeve connector 7*m* which has an outer diameter smaller than the inner diameter of each bending piece 7*k* so that the first area 7*a* and the second area 7*b* are connected via the tube sleeve connector 7*m*.

Furthermore, the bending piece 7*k* which is located closest to the proximal end side of the first area 7*a* and the bending piece 7*k* which is located closest to the distal end side of the second area 7*b* are each provided with a hole not shown, and each piece 7*k* is fastened to a screw hole, which is not shown and provided in the tube sleeve connector 7*m*, through the hole with a screw or the like not shown.

Referring back to FIG. 2, the plurality of bending pieces 7*k* located in the first area 7*a* are each provided with a wire guide 7*u* that holds, for example, four wires 30*u*, 30*d*, 30*r*, and 30*l* (see FIG. 15) inserted into the operation section 3 and the insertion portion 4.

Further, the distal end of each of the wires 30*u*, 30*d*, 30*r*, and 30*l* is fixed at a position which is shifted, for example, by 90° from each other in the circumferential direction of the bending portion 7 with respect to the bending piece 7*k* which is located closest to the distal end side in the insertion direction S out of the plurality of bending pieces 7*k*.

Further, each proximal end of the two wires 30*u* and 30*d* for up and down bending is, as shown in FIG. 4, wound around a sprocket 9*s* interconnected with the bending operation knob 9 via a chain not shown, and each proximal end of the two wires 30*r* and 30*l* for left and right bending is wound around a sprocket not shown and different from the sprocket 9*s* interconnected with the bending operation knob 9, via another chain not shown.

Further, as shown in FIG. 2, in the second area 7*b*, the distal end side of an interconnection member 33 is fixed to the bending piece 7*k* located closest to the proximal end side out of the plurality of bending pieces 7*k*, and the distal end side of the braid 8*h* making up the flexible tube portion 8 is fixed to the outer periphery of the proximal end side of the interconnection member 33. Further, the outer periphery of the braid 8*h* is covered by an outer skin tube 8*g*.

As shown in FIGS. 2 and 4, the outer periphery of each of the four wires 30*u*, 30*d*, 30*r*, and 30*l* inserted into the operation section 3 and the insertion portion 4 is covered respectively by inner coil sheath 40*u*, 40*d*, 40*r*, and 40*l* (see FIG. 7) which is a linear member made up of, for example, a soft coil pipe.

That is, in the operation section 3 and the insertion portion 4, four of the inner coil sheaths 40*u*, 40*d*, 40*r*, and 40*l* are inserted at positions shifted, for example, by 90° from one another in the circumferential direction of the insertion portion 4.

Note that each of the wires 30*u*, 30*d*, 30*r*, and 30*l* inserted into each of the inner coil sheaths 40*u*, 40*d*, 40*r*, and 40*l* is configured to be advanceable and retreatable with respect to the insertion direction S.

The reason why the inner coil sheaths 40*u*, 40*d*, 40*r*, and 40*l* are made up of soft coil pipes is that, if the outer periphery of each of the wires 30*u*, 30*d*, 30*r*, and 30*l* is covered by an ordinary rigid metal pipe, not only the bending portion 7 will not be bent, but also the flexibility of the flexible tube portion 8 will be reduced.

Therefore, the member for making up the inner coil sheaths 40*u*, 40*d*, 40*r*, and 40*l* is not be limited to the coil pipe, provided that the inner coil sheaths 40*u*, 40*d*, 40*r*, and 40*l* do not deteriorate the bending property of the bending portion 7 and the flexibility of the flexible tube portion 8, and can resist compressive force which acts along the extension direction of each of the inner coil sheaths 40*u*, 40*d*, 40*r*, and 40*l* when the bending portion 7 is bent.

Further, as shown in FIG. 2, distal ends 40*us*, 40*ds*, 40*rs*, and 40*ls* (40*ds*, 40*rs*, and 40*ls* are not shown) of the inner coil sheaths 40*u*, 40*d*, 40*r*, 40*l* are fixed to the bending piece 7*h* by, for example, brazing at a midpoint in the insertion direction S of the bending portion 7, for example, at the distal end position of the second area 7*b*.

Note that in the above-described configuration shown in FIG. 3, each of the distal ends 40*us*, 40*ds*, 40*rs*, and 40*ls* of the four inner coil sheaths 40*u*, 40*d*, 40*r*, and 40*l* is fixed to the tube sleeve connector 7*m* by, for example, brazing or the like.

Note that proximal ends 40*uk*, 40*dk*, 40*rk*, and 40*lk* (see FIG. 8, but 40*rk* and 40*lk* are not shown) of the inner coil sheaths 40*u*, 40*d*, 40*r*, and 40*l* are configured to be switchable between a fixed state and an unfixed state by a fixing mechanism 200 provided in the operation section 3. Note that the fixing mechanism 200 will be described below.

Further, as shown in FIGS. 2 and 4, the outer peripheries of the four inner coil sheaths 40u, 40d, 40r, and 40l located in the flexible tube portion 8 are respectively covered by outer coil sheaths 50u, 50d, 50r, and 50l (see FIG. 15), which are made of, for example, a soft coil pipe.

Note that each of the inner coil sheaths 40u, 40d, 40r, and 40l inserted in each of the outer coil sheaths 50u, 50d, 50r, and 50l is configured to be advanceable and retreatable with respect to the insertion direction S in a state in which each of the proximal ends 40uk, 40dk, 40rk, and 40lk is not fixed.

Further, each of the proximal ends 40uk, 40dk, 40rk, and 40lk is configured to be movable forwards and backwards in the insertion direction S following the motion forwards and backwards in the insertion direction S of each of the wires 30u, 30d, 30r, and 30l which is inserted into the interior portion, in the unfixed state.

Note that the outer peripheries of all of the four inner coil sheaths 40u, 40d, 40r, and 40l may not necessarily be covered by the outer coil sheaths 50u, 50d, 50r, and 50l and, for example, configuration may be such that only the outer periphery of the inner coil sheath 40u, which covers the outer periphery of the wire 30u that causes the bending portion 7 to bend in the UP direction, is covered by the outer coil sheath 50u.

The reason why the outer coil sheaths 50u, 50d, 50r, and 50l are made up of a soft coil pipe is that, if the outer periphery of the inner coil sheath 40u, 40d, 40r, and 40l is covered by an ordinary rigid metal pipe, the flexibility of the flexible tube portion 8 is deteriorated.

Therefore, the member for making up the outer coil sheaths 50u, 50d, 50r, and 50l is not limited to a coil pipe provided that the outer coil sheaths 50u, 50d, 50r, and 50l do not deteriorate the flexibility of the flexible tube portion 8 and can resist compressive force which acts along the extension direction of each of the outer coil sheaths 50u, 50d, 50r, and 50l when the bending portion 7 is bent. For example, the member may be a synthetic resin pipe which is strong in a compression direction and is bendable, or a metal pipe formed with a plurality of grooves and holes.

Further, as shown in FIG. 2, the distal ends 50us, 50ds, 50rs, and 50ls (distal ends 50ds, 50rs, and 50ls are not shown) of the outer coil sheaths 50u, 50d, 50r, and 50l are fixed, for example, by blazing, to the distal ends of the flexible tube portion 8, specifically, the proximal end side of the interconnection member 33.

Further, the proximal ends 50uk, 50dk, 50rk, 50lk are fixed, for example, by fitting rearward in the insertion direction S of the flexible tube portion 8, specifically to a fixing member 61 which is fixed to an outer casing 170 (see FIG. 16) provided in the operation section 3 so as to be movable forwards and backwards in the insertion direction S, as shown in FIGS. 4, 15, and 16.

Note that, as shown in FIGS. 15 and 16, for the purpose of decreasing the length of a grasping portion in the insertion direction S in the operation section 3, the fixing member 61 is preferably provided more forward than a treatment instrument insertion port 18 which is fixed with respect to the outer casing 170 by a fixing member 109.

Furthermore, as shown in FIG. 16, four long holes 105 are provided along the insertion direction S in the outer casing 170, thereby allowing the fixing member 61 to be moved forwards and backwards in the insertion direction S by using the long hole 105.

As the result of this, the position of the proximal ends 50uk, 50dk, 50rk, and 50lk of each of the outer coil sheaths 50u, 50d, 50r, and 50l can be moved forwards and backwards in the insertion direction via the long holes 105 so that the tension of the outer coil sheaths 50u, 50d, 50r, and 50l is made adjustable.

Further, as shown in FIG. 16, a notch 106 along the insertion direction for preventing the inner coil sheaths 40u, 40d, 40r, and 40l from touching the outer casing 170 is formed at the proximal end of the outer casing 170.

Furthermore, as shown in FIG. 15, a guide pipe 107 for preventing the inner coil sheaths 40u, 40d, 40r, and 40l from touching the fixing member 109 is also formed in the fixing member 109, to which the treatment instrument insertion port 18 is fixed.

Figure 19:
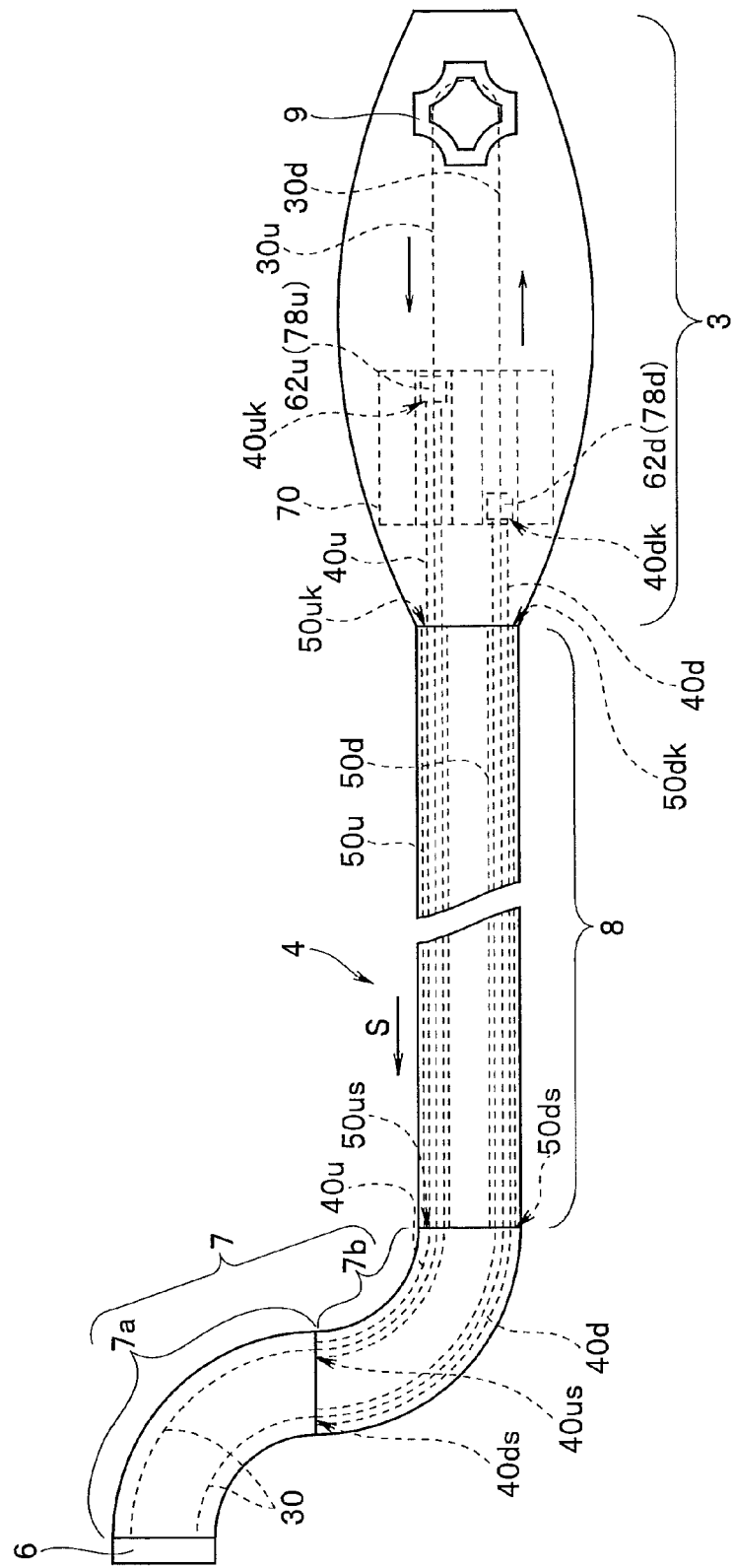
FIG. 19 is a diagram schematically showing a state in which the proximal end of the inner coil sheath of FIG. 17 is fixed, and the first area of the bending portion of FIG. 17 is bent in the opposite direction to the bending direction of the second area.

Note that the notch 106 and the guide pipe 107 are for the purpose of preventing the inner coil sheaths 40u, 40d, 40r, and 40l from hindering the movement in the insertion direction S of the inner coil sheaths 40u, 40d, 40r, and 40l by being hooked onto the outer casing 170 and the fixing member 109 in a state in which each of the proximal ends 40uk, 40dk, 40rk, and 40lk of the inner coil sheaths 40u, 40d, 40r, and 40l is not fixed, thus preventing that the bending shape of the second area 7b of the bending portion 7 shown in FIG. 19 descried later becomes unable to be fixed, as well as for the purpose of preventing damages of the inner coil sheaths 40u, 40d, 40r, and 40l which come into contact with the outer casing 170 and the fixing member 109.

Therefore, the guide pipe 107 may be provided, without being limited to in the fixing member 109, in other members with which the inner coil sheaths 40u, 40d, 40r, and 40l may come into contact in the insertion portion 4 and the operation section 3.

Since the outer coil sheaths 50u, 50d, 50r, and 50l are inserted into the flexible tube portion 8 with each of the distal ends 50us, 50ds, 50rs, and 50ls and each of the proximal ends 50uk, 50dk, 50rk, and 50lk being fixed, when any one of the wires 30u, 30d, 30r, and 30l is pulled to bend the bending portion 7 in either of up, down, left and right directions, the outer coil sheaths 50u, 50d, 50r, and 50l resist the compressive force which acts on the flexible tube portion 8 along the extension direction of the outer coil sheaths 50u, 50d, 50r, and 50l. As the result of this, the bending of the flexible tube portion 8, which has flexibility, along with the bending portion 7 is prevented.

Note that the lengths of the inner coil sheaths 40u, 40d, 40r, and 40l are formed into a length along the insertion direction S which prevents each of the proximal ends 40uk, 40dk, 40rk, and 40lk from being pulled toward the distal end side more than the proximal ends 50uk, 50dk, 50rk, and 50lk of the outer coil sheaths 50u, 50d, 50r, and 50l in a state in which each of the distal ends 40ls, 40ds, 40rs, and 40ls is fixed to the distal end of the second area 7b; and each of the distal ends 50us, 50ds, 50rs, and 50ls and each of the proximal ends 50uk, 50dk, 50rk, and 50lk of the outer coil sheath are fixed.

Further, each of the proximal end sides of the inner coil sheaths 40u, 40d, 40r, and 40l is inserted into below-described third grooves 73u, 73d, 73r, and 73l (see FIG. 7) formed in a below-described holding member 70 of the fixing mechanism 200 through an inner coil sheath guide 103 as shown in FIGS. 15 and 16.

Note that the inner coil sheath guide 103 has a function of guiding, along with the above-described guide pipe 107 and the notch 106, each proximal end side of the inner coil sheaths 40u, 40d, 40r, and 40l to be directly inserted into the third grooves 73u, 73d, 73r, and 73l.

As shown in FIGS. 4 and 7, stop members 62*u*, 62*d*, 62*r*, and 62*l* which are restricting members are respectively fixed to each of the proximal ends 40*uk*, 40*dk*, 40*rk*, and 40*lk* of the inner coil sheaths 40*u*, 40*d*, 40*r*, and 40*l*, and pipe members 75*u*, 75*d*, 75*r*, and 75*l* (the pipe member 75*r* is not shown) which cover the outer periphery of the wires 30*u*, 30*d*, 30*r*, and 30*l* are configured to extend rearward from the stop members 62*u*, 62*d*, 62*r*, and 62*l* (the stop member 62*l* is not shown), respectively.

In the outer peripheries of the pipe members 75*u*, 75*d*, 75*r*, and 75*l*, respective plurality of mobile bodies 78*u*, 78*d*, 78*r*, and 78*l* (the mobile body 78*r* is not shown) are provided in a state of being strung together along the insertion direction S.

To be specific, for example, seven mobile bodies, the mobile bodies 78*ua* to 78*uh*, are provided in a state of being strung together along the insertion direction S on the outer periphery of the pipe member 75*u*; for example, seven mobile bodies, the mobile bodies 78*da* to 78*dh*, are provided in a state of being strung together along the insertion direction S on the outer periphery of the pipe member 75*d*; for example, seven mobile bodies, the mobile bodies 78*ra* to 78*rh*, are provided in a state of being strung together along the insertion direction S on the outer periphery of the pipe member 75*r*; and for example, seven mobile bodies, the mobile bodies 78*la* to 78*lh*, are provided in a state of being strung together along the insertion direction S on the outer periphery of the pipe member 75*l*.

Note that, since the mobile bodies 78*uh*, 78*dh*, 78*rh*, and 78*lh* are respectively fixed to the vicinity of extension ends of the pipe members 75*u*, 75*d*, 75*r*, and 75*l*, the mobile bodies constitute restricting members. That is, the mobile bodies 78*uh*, 78*dh*, 78*rh*, and 78*lh* do not move forwards and backwards in the insertion direction S. Therefore, in the mobile bodies 78*u*, 78*d*, 78*r*, and 78*l*, the number of mobile bodies that actually move is six.

Mobile bodies 78*ua* to 78*ug*, 78*da* to 78*dg*, 78*ra* to 78*rg*, and 78*la* to 78*lg* are respectively configured to be rotatable in the circumferential direction C2 with respect to the outer periphery of each of the pipe members 75*u*, 75*d*, 75*r*, and 75*l*, and be movable forwards and backwards in the insertion direction S within a moving range M as shown in FIG. 7 between the stop members 62*u*, 62*d*, 62*r*, and 62*l* and the mobile bodies 78*uh*, 78*dh*, 78*rh*, and 78*lh*.

The reason why the mobile bodies 78*u*, 78*d*, 78*r*, and 78*l* are configured to be rotatable in the circumferential direction C2 is to facilitate the fitting of the below-described fixing pins 77*x* and 77*y* in between mobile bodies which are adjacent to each other in the insertion direction S in the mobile bodies 78*u*, 78*d*, 78*r*, and 78*l*.

Moreover, the reason why the mobile bodies 78*u*, 78*d*, 78*r*, and 78*l* are provided on the outer peripheries of pipe members 75*u*, 75*d*, 75*r*, and 75*l*, that is, why the mobile bodies are not provided directly on the outer peripheries of the wires 30*u*, 30*d*, 30*r*, and 30*l* is for the purpose of preventing that a force is applied to the wires by the fixing pins 77*x* and 77*y*, thereby disabling bending when the below-described fixing pins 77*x* and 77*y* fits in between the mobile bodies adjacent to each other in the insertion direction S in the mobile bodies 78*u*, 78*d*, 78*r*, and 78*l*, if the mobile bodies are provided directly on the outer periphery of the wires.

Therefore, the stop members 62*u*, 62*d*, 62*r*, and 62*l* and the mobile bodies 78*uh*, 78*dh*, 78*rh*, and 78*lh* have functions of restricting the movement of each of the mobile bodies 78*ua* to 78*ug*, 78*da* to 78*dg*, 78*ra* to 78*rg*, and 78*la* to 78*lg* with respect to the pipe members 75*u*, 75*d*, 75*r*, and 75*l* and preventing each mobile body 78*ua* to 78*ug*, 78*da* to 78*dg*, 78*ra* to 78*rg*, and 78*la* to 78*lg* from falling off from the pipe members 75*u*, 75*d*, 75*r*, and 75*l*.

Each of the mobile bodies 78*ua* to 78*uh*, 78*da* to 78*dh*, 78*ra* to 78*rh*, and 78*la* to 78*lh* is formed into a shape in which a crest portion 78*m* (see FIG. 9) is formed on the side face along the circumferential direction C2, for example, an abacus bead shape as shown in FIG. 8, specifically, a shape of trapezoidal revolving bodies having the same shape which are bonded in each bottom surface as shown in FIG. 8.

Thus, a valley portion 78*t* (see FIG. 8) is formed by slopes 78*ms* and 78*mk* (see FIG. 9) of the crest portion 78*m* along the insertion direction S between respective adjacent mobile bodies in the mobile bodies 78*u*, 78*d*, 78*r*, and 78*l*.

Next, the configuration of the fixing mechanism 200 on the proximal end side of the inner coil sheaths 40*u*, 40*d*, 40*r*, and 40*l* will be described.

As shown in FIG. 4, the fixing mechanism 200 is provided in the operation section 3, and has the holding member 70 which has a box-like shape as shown in FIG. 15 and holds a below-described moving member 74 and fixing pins 77*x* and 77*y*.

The holding member 70 is fitted with a moving member 74 along the insertion direction S as shown in FIG. 5 such that the moving member 74 is movable forwards and backwards in the insertion direction S from a below-described third position to a below-described fourth position, and is formed with a first groove 71 into which a part of the fixing pins 77*x* and 77*y* is fitted at a below described first position.

Note that the third position of the moving member 74 refers to a position at which the fixing pins 77*x* and 77*y* comes into abutment with the side face of a below-described first area 74*a* of the moving member 74 as shown in FIG. 4, and the fourth position refers to a position at which the fixing pins 77*x* and 77*y* comes into abutment with the side face of a below-described third area 74*c* of the moving member 74 as shown in FIG. 8.

Further, the first position of the fixing pins 77*x* and 77*y* refers to a position at which the fixing pins 77*x* and 77*y* is separated from the mobile bodies 78*u*, 78*d*, 78*r*, and 78*l*, and part of the fixing pins is fitted into the first groove 71, and comes into abutment with the side face of the first area 74*a* of the moving member 74.

Further, the holding member 70 is formed with second grooves 72*u*, 72*d*, 72*r*, and 72*l* (the second grooves 72*r*, 72*l* are not shown) which have a different direction from the insertion direction S, specifically, a set angle θ with respect to the insertion direction S as shown in FIG. 5.

Note that the second grooves 72*u*, 72*d*, 72*r*, and 72*l* are formed such that each of the entrances 72*ui*, 72*di*, 72*ri*, and 72*li* (the entrances 72*ri* and 72*li* are not shown) communicates with the first groove 71, and provides a groove into which a part of the fixing pins 77*x* and 77*y* is fitted at a first position.

Further, the holding member 70 is respectively formed with third grooves 73*u*, 73*d*, 73*r*, and 73*l* (see FIG. 7) passing through from the distal end to the proximal end of the holding member 70 along the insertion direction S.

The third grooves 73*u*, 73*d*, 73*r*, and 73*l* are formed so as to be in communication with each of the exits 72*ue*, 72*de*, 72*re*, and 72*le* (the exits 72*re* and 72*le* are not shown) of the second grooves 72*u*, 72*d*, 72*r*, and 72*l*, respectively.

The third groove 73*u* is a groove into which the inner coil sheath 40*u*, the stop member 62*u*, the pipe member 75*u*, and the mobile body 78*u* are fitted so as to be movable forwards and backwards in the insertion direction S, and into which a part of the fixing pin 77*x* coming out from the exit 72*ue* is fitted at a below-described second position.

Further, the third groove 73d is a groove into which the inner coil sheath 40d, the stop member 62d, the pipe member 75d, and the mobile body 78d are fitted so as to be movable forwards and backwards in the insertion direction S, and into which a part of the fixing pin 77y coming out from the exit 72de is fitted at a below-described second position.

Further, the third groove 73r is a groove into which the inner coil sheath 40r, the stop member 62r, the pipe member 75r, and the mobile body 78r are fitted so as to be movable forwards and backwards in the insertion direction S, and into which a part of the fixing pin 77x coming out from the exit 72re is fitted at the below-described second position.

Furthermore, the third groove 73l is a groove into which the inner coil sheath 40l, the stop member 62l, the pipe member 75l, and the mobile body 78l are fitted so as to be movable forwards and backwards in the insertion direction S, and into which a part of the fixing pin 77y coming out from the exit 72le is fitted at the below-described second position.

Note that the second position of the fixing pin 77x refers to a position at which a part of the fixing pin 77x is fitted in between mobile bodies adjacent in the insertion direction S in the mobile bodies 78u and 78r, in the third grooves 73u and 73r.

Further, the second position of the fixing pin 77y refers to a position at which a part of the fixing pin 77y is fitted in between mobile bodies adjacent in the insertion direction in the mobile bodies 78d and 78l, in the third grooves 73d and 73l.

The moving member 74 is caused to move rearward in the insertion direction S in the first groove 71 by a moving mechanism and moves from the third position to the fourth position, thereby causing the fixing pins 77x and 77y to move from the first position to the second position.

The principal part of the moving mechanism is made up of the fixing lever 80 shown in FIG. 1 described above and a link member 85, as shown in FIG. 4. Moreover, the moving mechanism is for pulling the moving member 74 with the link member 85 when the fixing lever 80 is rotated in one direction F1, thereby moving the moving member 74 from the third position to the fourth position in the first groove 71.

Moreover, when rotated in another direction F2, the fixing lever 80 presses forward the moving member 74 with the link member 85, thereby causing the moving member 74 to move from the fourth position to the third position in the first groove 71.

The moving member 74 has a wedge shape, as shown in FIG. 5, including a first area 74a having a first diameter d1, a second area 74c having a second diameter d2 larger than the first diameter d1, and a third area 74b interconnecting the first area 74a and the second area 74c along the insertion direction S.

Thus, the moving member 74 is moved from the third position to the fourth position in the first groove 71 by the moving mechanism, and thereby causing the fixing pins 77x and 77y, which are pressed to abut with the side face of the first area 74a at the first position by a return member not shown, to be moved to slide along the side face along the insertion direction S of the moving member 74 to the side face of the second area 74c through the slope 74bs formed on the side face of the third area 74b. That is, the moving member 74 causes the fixing pins 77x and 77y to move in a diameter expanding manner in the direction I perpendicular to the insertion direction S.

Note that the return member is for causing the fixing pins 77x and 77y to move to the first position while the moving member 74 is moving to the third position. That is, the fixing pins 77x and 77y are moved from the second position to the first position by the return member when the moving member 74 moves from the fourth position to the third position.

The moving member 74 moves the fixing pin 77x against the action of the return member from the first groove 71 to the third grooves 73u and 73r via the second grooves 72u and 72r, and thus to move from the first position to the second position. Further, the moving member 74 causes the fixing pin 77y to move against the action of the return member from the first groove 71 to the third groove 73d, 73l via the second groove 72d, 72l, and thus to move from the first position to the second position. As the result of this, the moving member 74 serves as a member for fitting a part of the fixing pins 77x and 77y, which partially comes out into the third grooves 73u, 73d, 73r, and 73l from each of the exits 72ue, 72de, 72re, and 72le of the second grooves 72u, 72d, 72r, and 72l, into a valley portion 78t between mobile bodies adjacent to each other in the insertion direction S as described above in the mobile bodies 78u, 78d, 78r, and 78l.

Further, as shown in FIG. 8, in a direction J (see FIG. 8) orthogonal to the insertion direction S and the direction I, a guide groove 76v for guiding the movement from the first position to the second position of the fixing pins 77x and 77y is formed in a cover member 70q provided on the surface of the side on which the third groove 73u, 73d of the holding member 70 is provided. Note that the guide groove 76v may be formed directly on the surface where the third groove 73u and 73d of the holding member 70 is formed, without being limited to the cover member 70q.

Further, as shown in FIG. 15, in the direction J, a guide groove 76w for guiding the movement of the fixing pins 77x and 77y from the first position to the second position on the plane 70t of the side where the third groove 73r and 73l of the holding member 70 is formed.

The guide grooves 76v and 76w, which have a substantially V-shape in plan view as shown in FIGS. 8 and 15, and a set angle θ described above with respect to the insertion direction S as shown in FIGS. 12 and 13, is made up of: a first areas 76va and 76wa (the first area 76wa is not shown) formed by being extended in a V-shape along the second grooves 72u, 72d, 72r, and 72l at a position overlapped with the second grooves 72u, 72d, 72r, and 72l; and a second areas 76vb and 76wb (the second area 78wa is not shown) extended rearward from the extension end of the first areas 76va and 76wa. Note that the second areas 76va and 76wb are formed into a groove having a larger width than that of the first areas 76va and 76wa.

The set angle θ between the first areas 76va and 76wa of the guide grooves 76v and 76w and the above-described second grooves 72u, 72d, 72r, and 73l is preferably set to be an angle at which the fixing pins 77x and 77y perpendicularly abut with the slope 78 ms of the crest portion 78m of the mobile body 78 as shown in FIG. 9.

This is because when the first areas 76va and 76wa of the guide grooves 76v and 76w and second grooves 72u, 72d, 72r, and 72l are formed into a set angle θ as shown in FIG. 10, since the fixing pins 77x and 77y obliquely abut with a mobile body, when, for example, the fixing pin 77x abuts with the mobile body 78dd obliquely with a set angle θ at a force P1 in the second position, a component force P2 for moving the mobile body 78dd rearward is generated from the force P1, it becomes easy to push away and move the mobile body 78dd.

Thus, as shown in FIG. 11, if the first areas 76va and 76wa of the guide grooves 76v and 76w and the second grooves 72u, 72d, 72r, and 72l are formed in a perpendicular direction I with respect to the insertion direction S, the fixing pin 77x will, for example, perpendicularly abut with the top portion of the crest portion 78m of the mobile body 78dd, and thus the moving force of the fixing pin 77x is absorbed by the mobile body 78dd and cannot be transformed into a force for moving the mobile body 78dd in the insertion direction S. Further, as the moving member 74 moves from the third position to the fourth position, the fixing pins 77x and 77y moving in the second grooves 72u, 72d, 72r, and 72l are made to abut with a forward wall surface of the second grooves 72u, 72d, 72r, and 72l, thus hindering smooth movement of the fixing pins 77x and 77y.

Because of this, the first areas 76va and 76wa of the guide grooves 76v and 76w, and the second grooves 72u, 72d, 72r, and 72l are formed with the set angle θ.

Further, the reason why the second areas 76vb and 76wb are formed in the guide grooves 76v and 76w is that if the guide grooves 76v' and 76w' are formed of the first areas 76v'a and 76w'a alone as shown in FIG. 14, when the fixing pins 77x and 77y are guided to the second position, the fixing pins 77x and 77y in contact with the top portion of the crest portion 78m of the mobile body 78 will become unknown whether to fall onto the forward side slope 78 ms side or to fall onto the rearward side slope 78mk side, thus hindering smooth movement of the fixing pins 77x and 77y.

That is, if the second areas 76vb and 76wb are formed, when, for example, the fixing pin 77x collides with, for example, the top portion of the crest portion 78m of the mobile body 78dd in the mobile body 78d at the second position as shown in FIG. 12, not only the fixing pin 77x becomes more likely to fall into the valley portion 78t on the forward slope 78 ms of the mobile body 78de, but also it becomes more likely to fall into the valley portion 78t on the rearward slope 78mk of the mobile body 78dc, thereby resulting in smooth movement of the fixing pin 77x. This is also true with the fixing pin 77y.

The fixing pins 77x and 77y, which have a circular column shape and are movably held between the first position and the second position by the holding member 70, are located between the first groove 73u and the first groove 73d, and between the first groove 73r and the first groove 73r in the direction I.

Further, the principal part of the fixing pins 77x and 77y is made up of a shaft body 77a having a circular column shape, and a rotating body 77b having a ring shape which is rotatably provided along the circumferential direction C1 on the outer periphery of the shaft body 77a.

The rotating body 77b is for facilitating, as it rotates, the fitting of the fixing pins 77x and 77y into the valley portion 78t between mobile bodies adjacent in the insertion direction S in the mobile bodies 78u, 78d, 78r, and 78l. This is because the sliding resistance of the rotating body 77b to the mobile body 78 is lowered in contact therewith when it rotates.

Further, the fixing pin 77x is configured, as shown in FIG. 8, such that each one end and each of the other ends in the direction J are engaged by, for example, E-rings 88u and 88r so that the slipping out of the rotating body 77b is prevented, and besides the rotating body 77b can be easily replaced by only detaching the E-rings 88u and 88r.

Further, the fixing pin 77y is configured, as shown in FIG. 8, such that each one end and each of the other ends in the direction J are engaged by, for example, E-rings 88d and 88l so that the slipping out of the rotating body 77b is prevented, and besides, the rotating body 77b can be easily replaced by only detaching the E-rings 88d and 88l.

The fixing pin 77x is guided to the guide grooves 76v and 76w when the moving member 74 is moved from the third position to the fourth position, and moves from the first groove 71 to the third groove 73u, 73r via the second grooves 72u and 72r so that a part of it is fitted into the valley portion 78t between any two mobile bodies adjacent to each other in the insertion direction S in the mobile bodies 78u and 78r at the second position as shown in FIG. 8.

The fixing pin 77y is guided to the guide grooves 76v and 76w when the moving member 74 is moved from the third position to the fourth position, and moves from the first groove 71 to the third grooves 73d and 73l via the second grooves 72d and 72l so that a part of it is fitted into the valley portion 78t between any two mobile bodies adjacent to each other in the insertion direction S in the mobile bodies 78d and 78l at the second position as shown in FIG. 8.

For example, as shown in FIG. 8, in the mobile body 78u, a part of the fixing pin 77x is fitted into the valley portion 78t which is formed between the mobile body 78uc and the mobile body 78ud by pushing away and moving the mobile body 78ud rearward by, for example, abutting with the forward slope 78ms of the crest portion 78m of the mobile body 78ud. In this occasion, a part of the fixing pin 77x is also fitted into the valley portion 78t between predetermined mobile bodies, though not shown, of the mobile body 78r.

Further, a part of the fixing pin 77y is fitted into the valley portion 78t which is formed between the mobile body 78da and the mobile body 78db by pushing away and moving the mobile body 78db rearward by, for example, abutting with the forward slope 78ms of the crest portion 78m of the mobile body 78db. In this occasion, a part of the fixing pin 77y is also fitted into the valley portion 78t between predetermined mobile bodies, though not shown, of the mobile body 78l.

Note that, after being fitted in between mobile bodies, the fixing pins 77x and 77y are fixed in position in the insertion direction by the second grooves 72u, 72d, 72r, and 72l. That is, after being fitted in between mobile bodies, the fixing pins 77x and 77y will not move forwards and backwards with the mobile body in the insertion direction S.

Further, after being fitted in between mobile bodies, as shown in FIG. 8, the fixing pins 77x and 77y press the mobile bodies 78ua, 78da, 78ra, and 78la against the stop members 62u, 62d, 62r, and 62l, respectively and press the mobile bodies 78ug, 78dg, 78rg, and 78lg against the mobile bodies 78uh, 78dh, 78rh, and 78lh, respectively. That is, the spacing between mobile bodies in the insertion direction S becomes zero, and the mobile bodies become unable to move forwards and backwards in the insertion direction S.

This is because the diameters of the fixing pins 77x and 77y to be fitted in between mobile bodies correspond to a moving range M in the insertion direction S of the mobile bodies 78ua to 78ug, 78da to 78dg, 78ra to 78rg, and 78la to 78lg.

As a result of that, the movement of the mobile body 78 is fixed by the fixing pins 77x and 77y. That is, the movement of the proximal end side of the inner coil sheaths 40u, 40d, 40r, and 40l is fixed.

Next, the fixing operation of the proximal end side of the inner coil sheaths 40u, 40d, 40r, and 40l by using the fixing mechanism 200 described above will be described in a brief summary.

When the proximal end side of the inner coil sheaths 40u, 40d, 40r, and 40l is fixed, first, the operator rotates the fixing lever 80 in one direction F1 as shown in FIG. 4.

As a result of that, the moving member 74 which is located at the third position in the first groove 71 is moved to the fourth position by the link member 85.

In this occasion, at the third position, the fixing pins 77x and 77y at the first position, which are pressed against the side face of the first area 74a by the return member not shown, are guided by the guide grooves 76v and 76w shown in FIGS. 8 and 15, by being moved to slide to the side face of the third area 74c via the slope 74bs of the second area 74b, and are fitted into the second grooves 72*u*, 72*d*, 72*r*, and 72*l* from the first groove 71 via the entrances 72*ui*, 72*di*, 72*ri*, and 72*li* and a part thereof being fitted into the third grooves 73*u*, 73*d*, 73*r*, and 73*l* via exits 72*ue*, 72*de*, 72*re*, and 72*le* to move to the second position.

At this second position, the fixing pins 77*x* and 77*y* fit into the valley portion 78*t* between predetermined adjacent mobile bodies in the mobile bodies 78*u*, 78*d*, 78*r*, and 78*l*, and push away the mobile bodies 78*u*, 78*d*, 78*r*, and 78*l* to move them by a moving range M. This results in that the fixing pins 77*x* and 77*y* press the mobile bodies 78*ua*, 78*da*, 78*ra*, and 78*la* against the stop members 62*u*, 62*d*, 62*r*, and 62*l*, and press the mobile bodies 78*ug*, 78*dg*, 78*rg*, and 78*lg* against the mobile bodies 78*uh*, 78*dh*, 78*rh*, and 78*lh* which are fixed to the pipe members 75*u*, 75*d*, 75*r*, and 75*l*.

As a result of that, the movement of the mobile body 78 is fixed so that the proximal end side of the inner coil sheaths 40*u*, 40*d*, 40*r*, and 40*l* is fixed.

Figure 17:
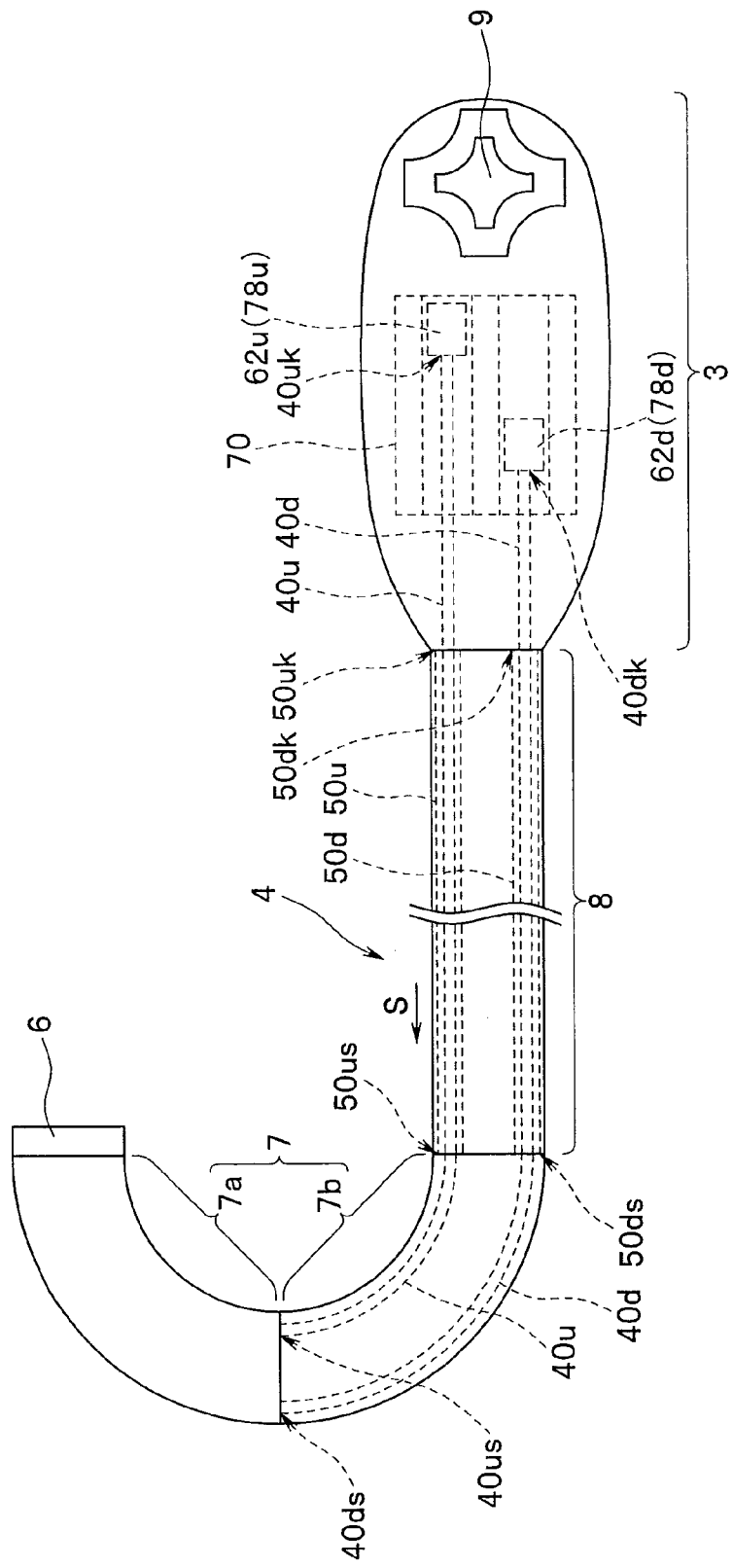
FIG. 17 is a diagram schematically showing a state in which in the bending portion of FIG. 2, the bending portion is bent from the proximal end side of the second area.
Figure 18:
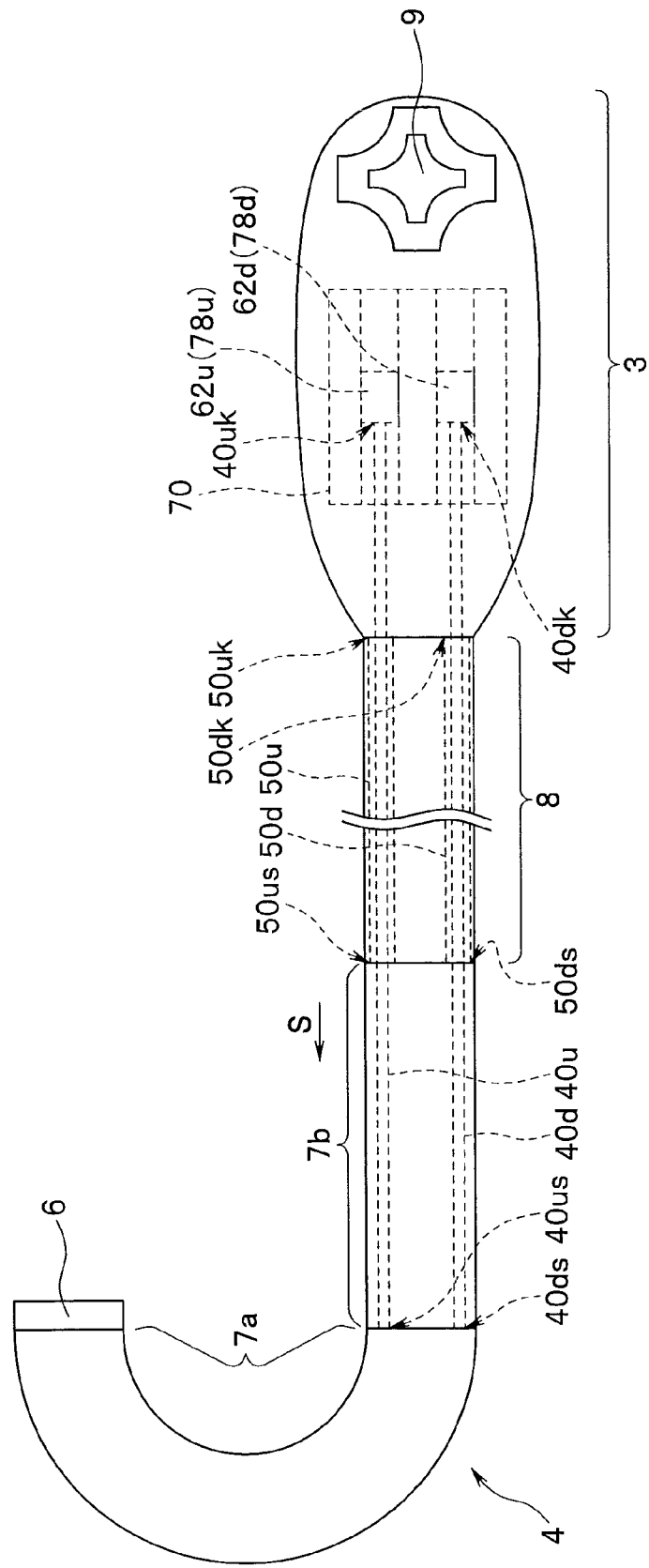
FIG. 18 is a diagram schematically showing a state in which the bending portion of FIG. 2 is bent from the proximal end side of the first area.

Next, the operation of the present embodiment will be described by using FIGS. 17 to 19. FIG. 17 is a diagram schematically showing a state in which in the bending portion of FIG. 2, the bending portion is bent from the proximal end side of the second area, and FIG. 18 is a diagram schematically showing a state in which the bending portion is bent from the proximal end side of the first area in the bending portion of FIG. 2.

Further, FIG. 19 is a diagram schematically showing a state in which the proximal end of the inner coil sheath of FIG. 17 is fixed, and the first area of the bending portion of FIG. 17 is bent in the opposite direction to the bending direction of the second area.

First, when the bending portion 7 is intended to be bent from the proximal end side of the second area 7*b*, that is, the entire bending portion 7 is intended to be bent, the operator releases the fixing of the proximal ends 40*uk*, 40*dk*, 40*rk*, and 40*lk* of the inner coil sheaths 40*u*, 40*d*, 40*r*, and 40*l* by use of the fixing mechanism 200 without performing the operation of the fixing lever 80.

In this state, if the operator operates a bending operation knob 9 to pull, for example, the wire 30*u* out of the four wires 30*u*, 30*d*, 30*r*, and 30*l*, the inner coil sheaths 40*u*, 40*d*, 40*r*, and 40*l* cannot resist the compressive force which acts along the extension direction of the inner coil sheaths 40*u*, 40*d*, 40*r*, and 40*l* at the second area 7*b* of the bending portion 7 since the proximal ends 40*uk*, 40*dk*, 40*rk*, and 40*lk* are not fixed so that the proximal end 40*dk* of the inner coil sheath 40*d* moves forward as the proximal end 40*uk* of the inner coil sheath 40*u* moves rearward.

Further, in the flexible tube portion 8, since the outer coil sheaths 50*u*, 50*d*, 50*r*, and 50*e* are fixed at the distal ends 50*us*, 50*ds*, 50*rs*, and 50*ls* and the proximal ends 50*uk*, 50*dk*, 50*rk*, and 50*lk*, the outer coil sheaths 50*u*, 50*d*, 50*r*, and 50*e* resist the compressive force which acts along the extension direction of the outer coil sheaths 50*u*, 50*d*, 50*r*, and 50*e*.

As a result of that, in the bending portion 7, the first area 7*a* and the second area 7*b* bend upward from the proximal end side of the second area 7*b* with the distal end of the outer coil sheaths 50*u*, 50*d*, 50*r*, and 50*e* as the starting point as shown in FIG. 17. That is, the entire bending portion 7 bends upward.

Next, when only the first area 7*a* is intended to be bent in the bending portion 7, the operator performs the operation of the fixing lever 80 as shown in FIG. 18 to fix the proximal ends 40*uk*, 40*dk*, 40*rk*, and 40*lk* of the inner coil sheaths 40*u*, 40*d*, 40*r*, and 40*l* by using the fixing mechanism 200 as described above.

In this state, if the operator operates the bending operation knob 9 to pull, for example, the wire 30*u* out of the four wires 30*u*, 30*d*, 30*r*, and 30*l*, the inner coil sheaths 40*u*, 40*d*, 40*r*, and 40*l* resist the compressive force that acts along the extension direction of the inner coil sheaths 40*u*, 40*d*, 40*r*, and 40*l* in the second area 7*b* of the bending portion 7 since the proximal ends 40*uk*, 40*dk*, 40*rk*, and 40*lk* are fixed.

As a result of that, in the bending portion 7, only the first area 7*a* bends upward from the proximal end side of the first area 7*a* with the distal ends of the inner coil sheaths 40*u*, 40*d*, 40*r*, and 40*l* as the starting points.

Further if the wire 30*u* is pulled in a state in which the proximal ends 40*uk*, 40*dk*, 40*rk*, and 40*lk* of the inner coil sheaths 40*u*, 40*d*, 40*r*, and 40*l* are not fixed, the first area 7*a* and the second area 7*b* bend upward as described above and shown in the above-described FIG. 17.

Thereafter, if the proximal ends 40*uk*, 40*dk*, 40*rk*, and 40*lk* of the inner coil sheaths 40*u*, 40*d*, 40*r*, and 40*l* are fixed by using the fixing mechanism 200 in a state in which the proximal end side of the inner coil sheath 40*u* is moved rearward, and the proximal end side of the inner coil sheath 40*d* is moved forward, and the wire 30*d* is pulled, only the first area 7*a* bends downward, opposite to upward, from the proximal end side with the upward bending shape of the second area 7*b* being fixed, since the proximal ends 40*uk*, 40*dk*, 40*rk*, and 40*lk* are fixed as shown in FIG. 19.

Further, since the bending shape of the second area 7*b* is fixed by the above-described fixing mechanism 200, the bending shape is not released.

Further, the bending direction is not limited to upward and downward directions. That is, the first area 7*a* may be bent in a leftward or rightward direction with the second area 7*b* being bent in an upward direction, by pulling respectively corresponding wires 30, and besides, the first area 7*a* may be bent in any of upward, downward, leftward, and rightward directions which is different from the bending direction of the second area 7*b* with the second area 7*b* being bent in any of upward, downward, leftward, and rightward directions.

According to such a configuration as shown in FIG. 19, since the first area 7*a* and the second area 7*b* can be bent in different directions, such an effect can be expected that it becomes easy to perform observation and treatment at a location where a frontal view of a lesion is hard to be obtained, such as the cardiac orifice of the stomach, a portion of the rectum near the rear side of the anus, the rear side of folds in the large intestine, and the like, as well as that the practitioner can operate with only one hand.

In this way, in the present embodiment, it has been described that the proximal end side of the inner coil sheaths 40*u*, 40*d*, 40*r*, and 40*l* is fixed by the fixing mechanism 200.

Specifically, it has been described that mobile bodies 78*ua* to 78*ug*, 78*da* to 78*dg*, 78*ra* to 78*rg*, and 78*la* to 78*lg* which are movable forwards and backwards in the insertion direction S by a moving range M between the stop members 62*u*, 62*d*, 62*r*, and 62*l* and the mobile bodies 78*uh*, 78*dh*, 78*rh*, and 78*lh* are provided in the outer periphery of the pipe members 75*u*, 75*d*, 75*r*, and 75*l* provided on the proximal end side of the inner coil sheaths 40*u*, 40*d*, 40*r*, and 40*l*, and the fixing pins 77*x* and 77*y* which move from the first position to the second position by being guided by the guide grooves 76*v* and 76*w* as the moving member 74 moves from the third position to the fourth position, fit into the valley portion 78*t* between any two mobile bodies in the mobile bodies 78*ua* to 78*ug*, 78*da* to 78*dg*, 78*ra* to 78*rg*, and 78*la* to 78*lg*, thereby fixing the proximal end sides of the inner coil sheaths 40*u*, 40*d*, 40*r*, and 40*l*.

Moreover, it has been described that when the fixing pins 77*x* and 77*y* fit in between mobile bodies, the fixing pins 77*x* and 77y push away and cause the mobile bodies to move forwards and backwards in the insertion direction S by a moving range M.

Further, it has been described that the fixing pins 77x and 77y have the rotatable rotating body 77b in the circumferential direction C1 on its outer periphery, and mobile bodies 78ua to 78ug, 78da to 78dg, 78ra to 78rg, and 78la to 78lg are rotatable in the circumferential direction C2.

Further, it has been described that the fixing pins 77x and 77y are brought into oblique abutment with the mobile body by the second grooves 72u, 72d, 72r, and 72l of the guide grooves 76v and 76w.

According to this, the fixing pins 77x and 77y can be easily moved with a small amount of force from the first position to the second position by utilizing the principle of the lever only by moving the moving member 74 from the third position to the fourth position; in addition to that, since the rotating body 77b of the fixing pins 77x and 77y rotates as well as the mobile body 78 itself rotates, the fixing pins 77x and 77y smoothly fit in between mobile bodies; and furthermore, the mobile bodies are pushed away to move by a moving range M by the fitting of the fixing pins 77x and 77y so that a very small amount of operational force will be enough for the fixing lever 80.

Further, since the fixing pins 77x and 77y after being fitted in between mobile bodies press the mobile bodies 78ua, 78da, 78ra, and 78la against the stop members 62u, 62d, 62r, and 62l and press the mobile bodies 78ug, 78dg, 78rg, and 78lg against the mobile bodies 78uh, 78dh, 78rh, and 78lh, it is possible to securely fix the movement of the mobile bodies. That is, it is possible to securely fix the movement of the inner coil sheaths 40u, 40d, 40r, and 40l.

Moreover, the fixing of the proximal end sides of the inner coil sheaths 40u, 40d, 40r, and 40l can be performed in a one-touch operation only by rotating the fixing e lever 80 in the direction F1 as described above.

Further, in contrast to a configuration in which the proximal end sides of the inner coil sheaths 40u, 40d, 40r, and 40l are fixed by using friction force, since there is no member that causes wear, excellent durability is achieved without requiring maintenance work.

Further, since the rotating body 77b of the fixing pins 77x and 77y, which are in contact with a mobile body, is rotatable, and also the mobile body itself is rotatable, the contact point of the fixing pins 77x and 77y with respect to the mobile body will be different every time contact occurs, thus allowing the prevention of wear of the mobile bodies and the rotating body 77b.

Further, in contrast to a configuration in which the proximal end sides of the inner coil sheaths 40u, 40d, 40r, and 40l are fixed by using friction force, since there is no need of a member which comes into contact over a large area with a linear member to generate friction force, it is possible to reduce the sizes of the fixing mechanism 200 and the endoscope 2.

As so far described, it is possible to provide the endoscope 2 including the compact fixing mechanism 200, which is excellent in durability, and which can securely fix the positions on the proximal end sides of the inner coil sheaths 40u, 40d, 40r, and 40l in the insertion direction S with a small operation force and in a one-touch operation.

Figure 20:
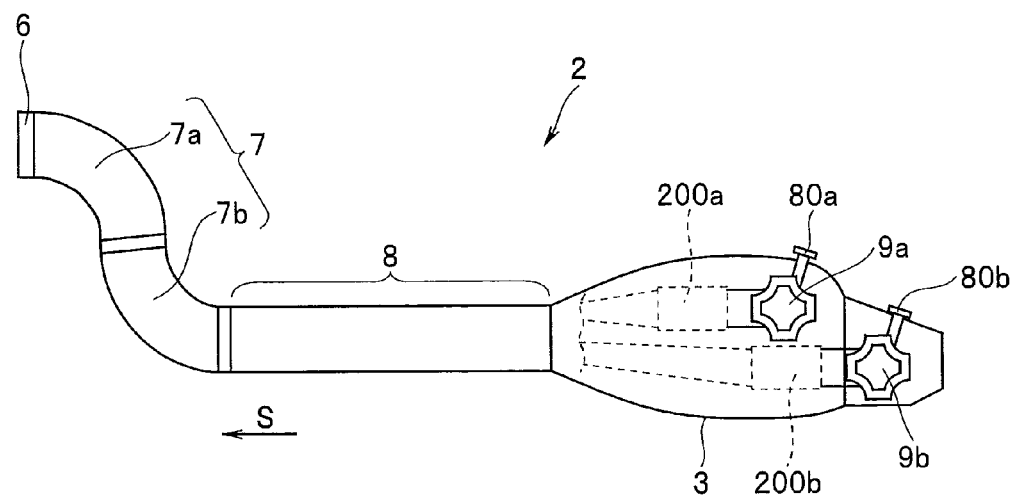
FIG. 20 is diagram of an endoscope showing a modification in which two levers, that is, levers for fixing the shapes of the first area and the second area of the bending portion are provided in the operation section.

Hereafter, modifications will be shown using FIG. 20. FIG. 20 is diagram of an endoscope showing a modification in which two levers, that is, levers for fixing the shapes of the first area and the second area of the bending portion are provided in the operation section.

As shown in FIG. 20, an endoscope 2 may have a configuration in which a fixing mechanism 200a for switching the fixing of the proximal end of coil sheaths fixed at the distal end of a first area 7a of a bending portion 7, and a fixing mechanism 200b for switching the fixing of the proximal end of coil sheaths fixed at the distal end of a second area 7b of the bending portion 7 are provided in an operation section 3, and the bending shape of the first area 7a and the bending shape of the second area 7b are fixed separately, or altogether by operating fixing lever 80a, 80b.

Note that in this configuration, mobile bodies 78u, 78d, 78r, and 78l may be provided for the wire for bending the first area 7a and the wire for bending the second area 7b, respectively.

Further, other modifications will be shown.

In the present embodiment, although a case is taken as an example in which the number of mobile bodies that actually move is set to be six between the stop members 62u, 62d, 62r, and 62l of the pipe members 75u, 75d, 75r, and 75l and the mobile bodies 78uh, 78dh, 78rh, and 78lh in the fixing mechanism 200, as the number of mobile bodies increases, and as the spacing between mobile bodies decreases, the fixing accuracy will be improved.

For example, in a configuration in which the proximal end sides of the inner coil sheaths 40u, 40d, 40r, and 40l are fixed, when the bending shape of the second area 7b of the bending portion 7 is fixed as shown in FIG. 19, the bending angle can be finely defined according to the number of mobile bodies. That is, the accuracy of fixing can be improved.

This is because, since the bending shape is fixed with the fixing pins 77x and 77y being fitted in between mobile bodies, when the number of mobile bodies is six, the bending angle can be fixed in six steps according to the fitting position of the fixing pins 77x and 77y; and when the number of mobile bodies is ten, the bending angle can be fixed in ten steps according to the fitting position of the fixing pins 77x and 77y.

To be more specific, suppose that the bending angle is 180°, the moving amount of the wire 30 is 10 mm at that time, the number of mobile bodies is 10, and the spacing between mobile bodies is 1 mm, since 180/10=18, the bending angle of the second area 7b can be fixed at every 18°, and suppose that the spacing between mobile bodies is 0.5 mm, and the number of mobile bodies is 20, since 180/20=9, the bending angle can be finely fixed at every 9°, thus improving the accuracy of fixing.

Figure 21:
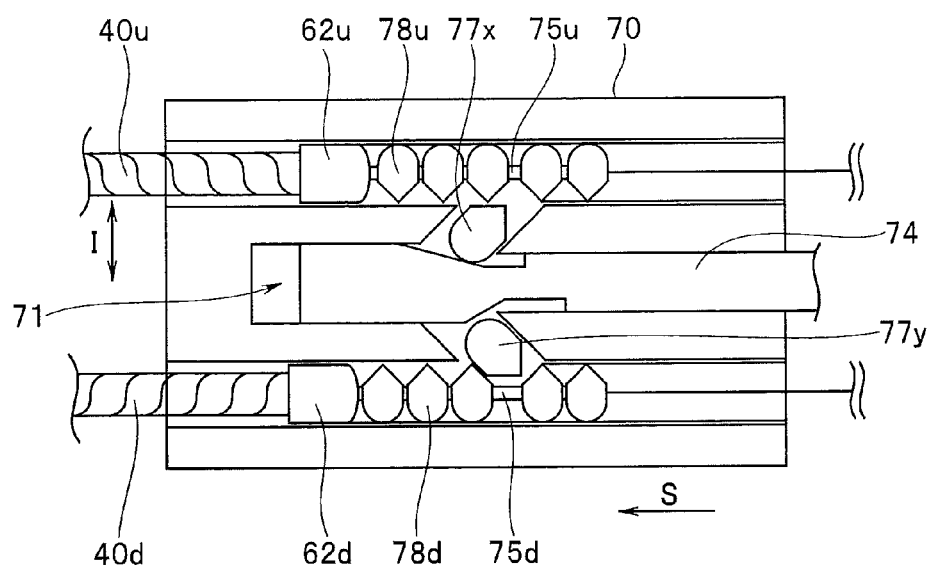
FIG. 21 is a diagram of a fixing mechanism showing a modification in which the shapes of the mobile body and the fixing pin are configured to differ from those of FIG. 4.
Figure 22:
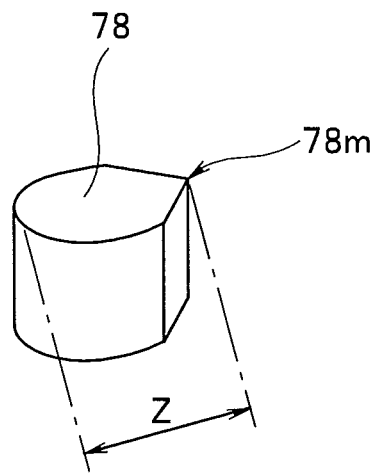
FIG. 22 is a perspective view enlargedly showing the mobile body of FIG. 21.

Further, another modification will be shown by using FIGS. 21 and 22. FIG. 21 is a diagram of a fixing mechanism showing a modification in which the shapes of the mobile body and the fixing pin are configured to differ from those of FIG. 4, and FIG. 22 is a perspective view enlargedly showing a mobile body of FIG. 21.

In the present embodiment described above, the mobile bodies 78ua to 78uh, 78da to 78dh, 78ra to 78rh, and 78la to 78lh are shown to have a shape in which the crest portion 78m (see FIG. 9) is formed on the side face along the circumferential direction C2, for example, an abacus bead shape as shown in FIG. 8.

Further, it has been shown that the mobile bodies 78ua to 78ug, 78da to 78dg, 78ra to 78rg, and 78la to 78lg are rotatable in the circumferential direction C2, and these results in a configuration which is resistant to wear even if the fixing pins 77x and 77y come into contact therewith.

However, in the configuration in which the mobile bodies are rotatable in the circumferential direction C2, in consideration of the rotation radius, since the positions of a cover member 70q (see FIG. 8) and a plane 70t (see FIG. 15) of the holding member 70 in the direction J are specified such that the mobile bodies will not come into contact with the cover member 70*q* and the plane 70*t*, a problem exists in that the size of the fixing mechanism 200 increases in the direction J.

In view of the above-described problems, as shown in FIGS. 21 and 22, each mobile body 78*ua* to 78*ug*, 78*da* to 78*dg*, 78*ra* to 78*rg*, and 78*la* to 78*lg* may have a tear-drop shape in plan view with a sharp crest portion 78*m* in the shape in which the crest portion 78*m* (see FIG. 9) is formed on the side face along the circumferential direction C2, and may be configured to be movable forwards and backwards in the insertion direction S, but not rotatable in the circumferential direction C2.

Moreover, in this case, to improve the durability of mobile bodies 78, the mobile bodies 78 are treated with diamond-like coating, nitriding treatment, and the like on the outer surface thereof.

According to such a configuration, since there is no need of rotating the mobile bodies 78, the width Z of the mobile body 78 in the direction I orthogonal to the insertion direction S can be decreased as shown in FIG. 22, and further the distance in the direction J between the mobile body 78 and the cover member 70*q* or the plane 70*t* can be decreased, it is possible to reduce the size of the fixing mechanism 200.

Furthermore, although in the present embodiment, the fixing pins 77*x* and 77*y* are shown to have a circular column shape, the fixing pins 77*x* and 77*y* may have, without being limited to that, a tear-drop shape in which the area to be fitted in between mobile bodies is sharpened as with the mobile bodies as shown in FIG. 21, and may be any shape provided that it can be fitted in between mobile bodies.

Figure 23:
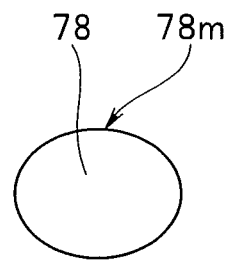
FIG. 23 is a diagram showing a modification in which the mobile body of FIG. 4 is formed into a sphere.
Figure 24:
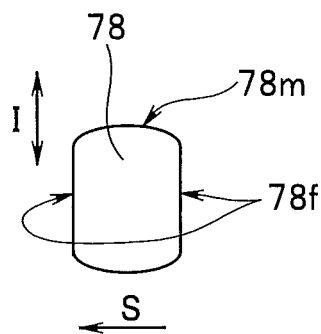
FIG. 24 is a diagram showing a modification in which the mobile body of FIG. 4 is formed into a shape having a plane in a direction orthogonal to the insertion direction.
Figure 25:
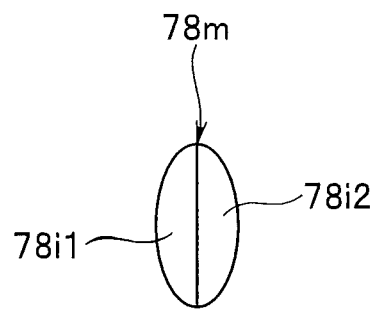
FIG. 25 is a diagram showing a modification in which the mobile body of FIG. 4 is formed into a biconvex lens shape.

Further, hereinafter, another modification will be shown by using FIGS. 23 to 25. FIG. 23 is a diagram showing a modification in which the mobile body of FIG. 4 is formed into a sphere; FIG. 24 is a diagram showing a modification in which the mobile body of FIG. 4 is formed into a shape having a plane in a direction orthogonal to the insertion direction; and FIG. 25 is a diagram showing a modification in which the mobile body of FIG. 4 is formed into a biconvex lens shape.

In the present embodiment described above, each of the mobile bodies 78*ua* to 78*uh*, 78*da* to 78*dh*, 78*ra* to 78*rh*, and 78*la* to 78*lh* is shown to have a shape in which the crest portion 78*m* (see FIG. 9) is formed on the side face along the circumferential direction C2, for example, an abacus bead shape as shown in FIG. 8.

Without being limited to the above-described shape, the mobile body 78 may be formed into a sphere as shown in FIG. 23, or may be formed into a shape having a plane 78*f* in the direction I orthogonal to the insertion direction S as shown in FIG. 24, provided that the crest portion 78*m* is formed on the side face thereof. Further, the mobile body may be formed into, for example, a biconvex lens shape in which members 78*i*1 and 78*i*2 having a convex lens shape are bonded to each other as shown in FIG. 25, more specifically, a shape in which two portions of a sphere cut off in a straight line at a position not passing through the center of the sphere are bonded together in the sectioned plane, that is, an oblate spheroidal shape, or formed into any other shapes.

Further, provided that the fixing pins 77*x* and 77*y* can be fitted in between mobile bodies, the mobile body 78 may have a shape in which no crest portion 78*m* is formed on the side face thereof.

Note that, although in the present embodiment, the linear member has been shown by taking an example of the inner coil sheaths 40*u*, 40*d*, 40*r*, and 40*l*, other linear members, without being limited to that, may of course be used provided that they are movable forwards and backwards in the insertion direction S in the insertion portion of the endoscope.

For example, the linear member may be the above-described wires 30*u*, 30*d*, 30*r*, and 30*l*; a coil pipe wire to be pulled/released to make the rigidity of a coil pipe variable in a coil pipe for making the rigidity of the flexible tube portion 8 variable in the insertion portion 4; an operation wire to be pulled/released for a raising or lowering operation of a treatment instrument elevator in the distal end portion 6 of the insertion portion 4; and the like.

In this case, the movement of the linear member may be fixed by providing a plurality of mobile bodies along the insertion direction S in a state of being strung together on these linear members, and fitting the fixing pin in between mobile bodies as with the present embodiment.

Further, although in the present embodiment, a configuration in which a moving member 43 is moved from the third position to the fourth position by being moved rearward, and thereby the fixing pins 77*x* and 77*y* are moved from the first position to the second position is shown as an example, without being limited to that, it goes without saying that the configuration may be such that the moving member 43 is moved from the third position to the fourth position by being moved forward, and thereby the fixing pins 77*x* and 77*y* are moved from the first position to the second position.

Furthermore, although in the present invention, it has been shown that the proximal ends of the four inner coil sheaths 40*u*, 40*d*, 40*r*, and 40*l* are fixed by two fixing pins 77*x* and 77*y*, the number of the linear members is arbitrary, and also the number of the fixing pins may be changed according to the number of the linear members.

Further, although in the present embodiment, the insertion device is shown by taking an example of an endoscope including two bending portions, the insertion device may be an endoscope including one bending portion, and also the insertion device of the present embodiment may be applied, without being limited to endoscopes, other insertion devices such as guide tubes, various treatment instruments having no observation means, manipulators, and the like.

What is claimed is:

1. An insertion device including an elongated insertion portion to be inserted into a subject, comprising:
    a linear member inserted into the insertion portion and movable forwards and backwards in an insertion direction of the insertion portion;
    a plurality of mobile bodies provided in a state of being strung together along the insertion direction on an outer periphery of the linear member, the mobile bodies being movable forwards and backwards in the insertion direction with respect to the linear member;
    a restricting member fixed with respect to the linear member, the restricting member restricting a movable range of each of the mobile bodies with respect to the linear member, and preventing each of the mobile bodies from falling off from the linear member; and
    a fixing pin being movable between a first position separated from the plurality of mobile bodies, and a second position at which the fixing pin is fitted in between any two of the mobile bodies adjacent to each other in the insertion direction, and being fixed in position in the insertion direction after being fitted in between the mobile bodies at the second position, the fixing pin being formed such that a diameter of an area to be fitted in between the mobile bodies coincides with the movable range of the mobile bodies.

2. The insertion device according to claim 1, further comprising:

a holding member for holding the fixing pin so as to be movable between the first position and the second position; and a guide groove for guiding the fixing pin from the first position to the second position, the guide groove being formed in the holding member so as to have a set angle with respect to the insertion direction, wherein the plurality of the mobile bodies each have a shape in which a crest portion is formed on a side face along a circumferential direction of the linear member in each of the mobile bodies, and the fixing pin is brought into abutment with a slope of the crest portion of any one of the mobile bodies by the guide groove to move the mobile body in abutment therewith and fit in between the mobile bodies at the second position.

3. The insertion device according to claim 2, wherein the set angle of the guide groove is set at an angle at which the fixing pin is perpendicularly abutted with the slope of the crest portion of the mobile body at the second position.

4. The insertion device according to claim 1, further comprising a moving member for moving the fixing pin from the first position to the second position.

5. The insertion device according to claim 4, further comprising:

a holding member for holding the moving member and the fixing pin; and a moving mechanism for moving the moving member forward or rearward in the insertion direction with respect to the holding member from a third position to a fourth position, wherein as the moving member is moved from the third position to the fourth position by the moving mechanism, the moving member moves the fixing pin in contact with the moving member in a direction different from the insertion direction from the first position to the second position to cause the fixing pin to be fitted in between the mobile bodies.

6. The insertion device according to claim 5, wherein the holding member is provided with a return member for moving the fixing pin to the first position when the moving member is moving to the third position.

7. The insertion device according to claim 6, wherein the holding member comprises:

a first groove along the insertion direction, wherein the moving member is fitted into the first groove so as to be movable between the third position and the fourth position, and a part of the fixing pin is fitted into the first groove at the first position;

a second groove formed in a direction different from the insertion direction, wherein an entrance of the second groove is in communication with the first groove and the fixing pin is fitted into and moves in the second groove; and a third groove along the insertion direction in communication with an exit of the second groove, wherein the linear member, each of the mobile bodies, and the restricting member are fitted into the third groove so as to be movable forwards and backwards in the insertion direction, and a part of the fixing pin is fitted into the third groove at the second position, wherein as the moving member is moved in the first groove by the moving mechanism from the third position to the fourth position, the moving member moves the fixing pin from the first groove to the third groove via the second groove against an action of the return member and from the first position to the second position to cause the fixing pin, a part of which projects into the third groove from the exit of the second groove, to be fitted in between the mobile bodies.

8. The insertion device according to claim 7, wherein the second groove is formed along the set angle.

9. The insertion device according to claim 7, wherein the moving member comprises a first area having a first diameter, a second area having a second diameter larger than the first diameter, and a third area interconnecting the first area and the second area along the insertion direction, wherein the moving member moves from the third position to the fourth position so that in the first groove the fixing pin, which is pressed to abut with the moving member by the return member, is moved to slide from the first area to the second area via the third area to cause the fixing pin to be moved from the first position to the second position.

10. The insertion device according to claim 7, wherein the holding member is formed with a guide groove along the second groove, the guide groove guiding the fixing pin from the first position to the second position.

11. The insertion device according to claim 1, wherein each of the mobile bodies is rotatable in a circumferential direction of the linear member with respect to the linear member.

12. The insertion device according to claim 2, wherein a plurality of valley portions are formed between the adjacent respective mobile bodies along the insertion direction by the crest portion of each of the mobile bodies, and the fixing pin is fitted into any one of the valley portions at the second position.

13. The insertion device according to claim 1, wherein the fixing pin is provided with a rotating body rotatable in a circumferential direction of the fixing pin on an outer periphery of the fixing pin.

* * * * *